(12) United States Patent
Judson

(10) Patent No.: US 12,011,574 B2
(45) Date of Patent: Jun. 18, 2024

(54) MEDICATION DELIVERY DEVICE WITH GEAR SET DOSAGE SYSTEM

(71) Applicant: Eli Lilly and Company, Indianapolis, IN (US)

(72) Inventor: Jared Alden Judson, Medford, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 260 days.

(21) Appl. No.: 17/508,494

(22) Filed: Oct. 22, 2021

(65) Prior Publication Data

US 2022/0040415 A1 Feb. 10, 2022

Related U.S. Application Data

(63) Continuation of application No. 17/044,401, filed as application No. PCT/US2020/023514 on Mar. 19, 2020, now Pat. No. 11,179,522.

(60) Provisional application No. 62/826,232, filed on Mar. 29, 2019.

(51) Int. Cl.
*A61M 5/315* (2006.01)

(52) U.S. Cl.
CPC .... *A61M 5/31551* (2013.01); *A61M 5/31541* (2013.01); *A61M 5/31568* (2013.01); *A61M 2205/50* (2013.01)

(58) Field of Classification Search
None
See application file for complete search history.

(56) References Cited

U.S. PATENT DOCUMENTS

| | | | |
|---|---|---|---|
| 6,663,602 B2 | 12/2003 | Moller et al. | |
| 7,517,334 B2 | 4/2009 | Jacobs et al. | |
| 7,857,791 B2 | 12/2010 | Jacobs et al. | |
| 8,202,255 B2 * | 6/2012 | Saiki | A61M 5/31563 604/207 |
| 8,361,026 B2 | 1/2013 | Edwards et al. | |
| 9,707,354 B2 | 7/2017 | Madsen et al. | |
| 11,179,522 B2 * | 11/2021 | Judson | A61M 5/31575 |
| 2007/0197976 A1 | 8/2007 | Jacobs et al. | |

(Continued)

OTHER PUBLICATIONS

Patent Cooperation Treaty International Search Report pertaining to International Application No. PCT/US2020/023514; International Filing Date: Mar. 19, 2020; dated Jul. 27, 2020.

(Continued)

*Primary Examiner* — Manuel A Mendez
(74) *Attorney, Agent, or Firm* — M. Daniel Spillman

(57) ABSTRACT

A medication delivery device is disclosed including a rack-and-pinion plunger drive system. The drive system includes an output drive having a pawled end movably coupled with the ratchet teeth of the plunger, and a pinion drive coupled between the housing, the output drive and an actuator. Actuator is longitudinally movable between dose set and delivery positions. Movement of the actuator causes rotation of the pinion drive along the rack to translate the output drive member with the pawled end that is engaged with the plunger ratchet teeth to distally advance the plunger. The device may include one or more of an end of dose mechanism to limit travel of the actuator, a load brake system to stop travel of the plunger under high input forces, a dose detection system, and a dose selector to vary the amount of dose set.

20 Claims, 16 Drawing Sheets

(56) References Cited

U.S. PATENT DOCUMENTS

2010/0137792 A1    6/2010   Boyd et al.
2018/0064882 A1    3/2018   Judson
2019/0028276 A1   12/2019   Wilson et al.

OTHER PUBLICATIONS

Patent Cooperation Treaty Written Opinion of the International Searching Authority pertaining to International Application No. PCT/US2020/023514; International Filing Date: Mar. 19, 2020; dated Jul. 27, 2020.

* cited by examiner

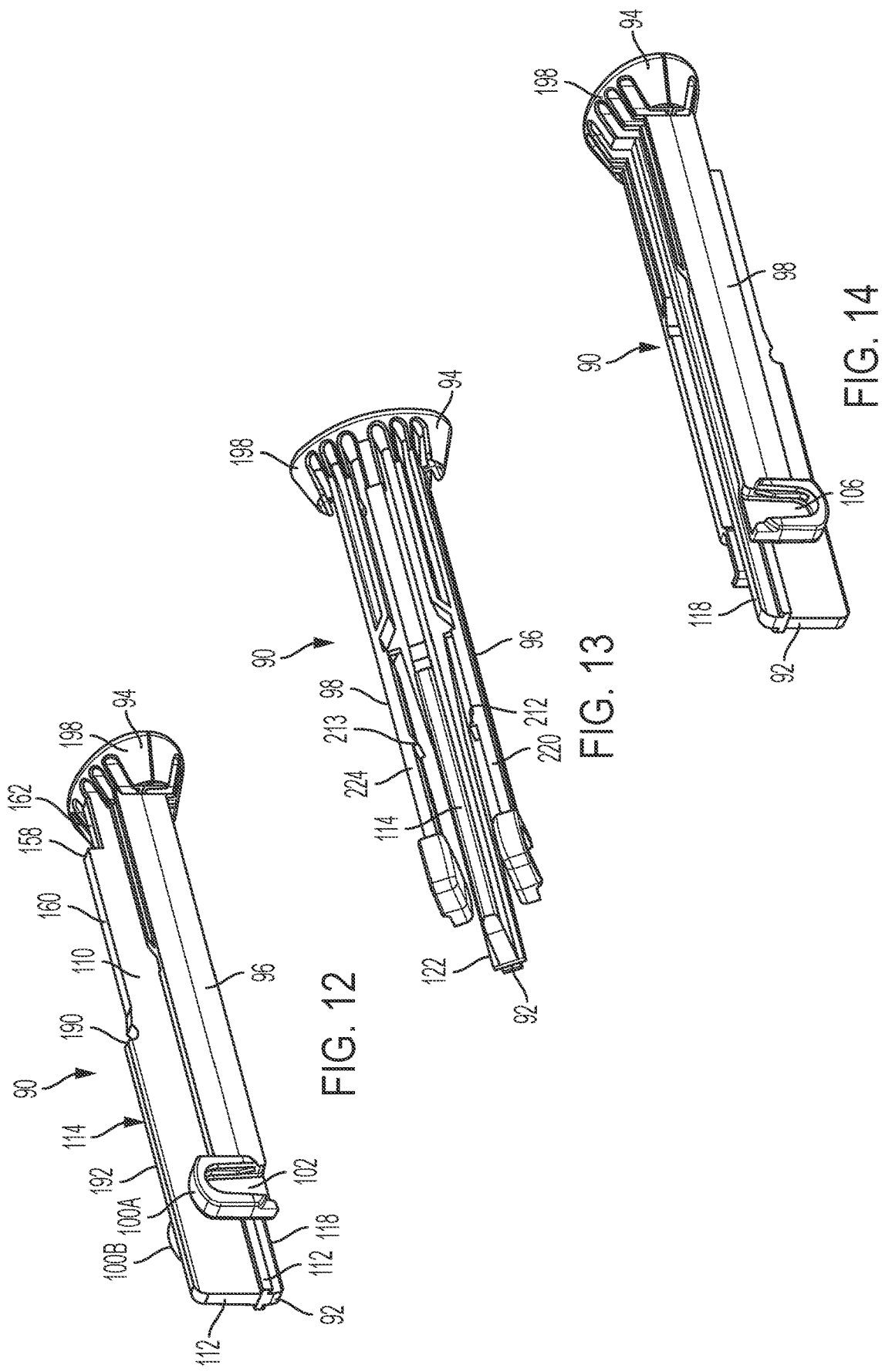

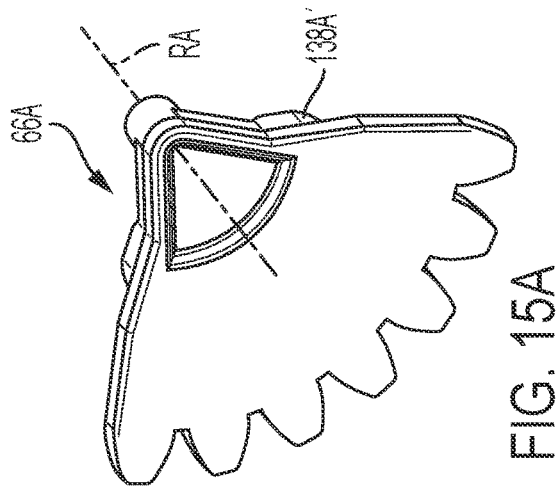
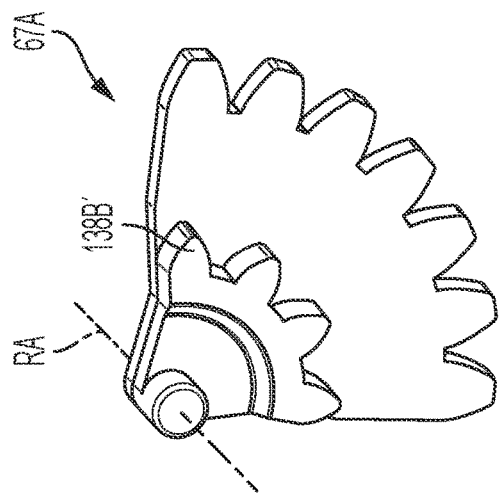
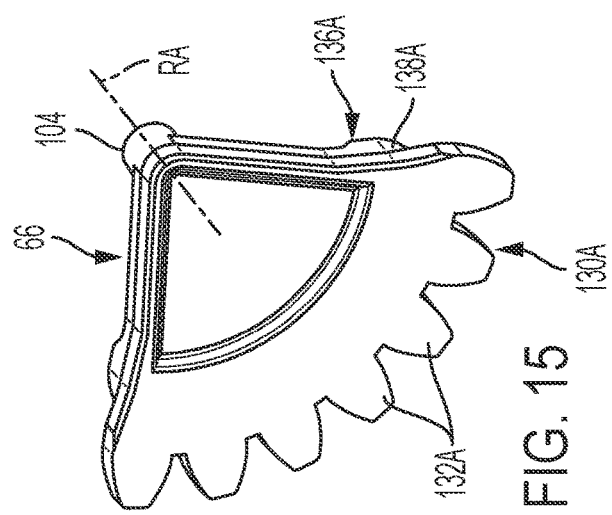
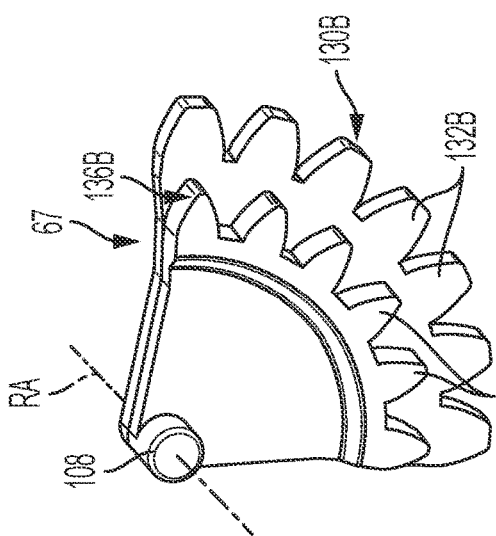

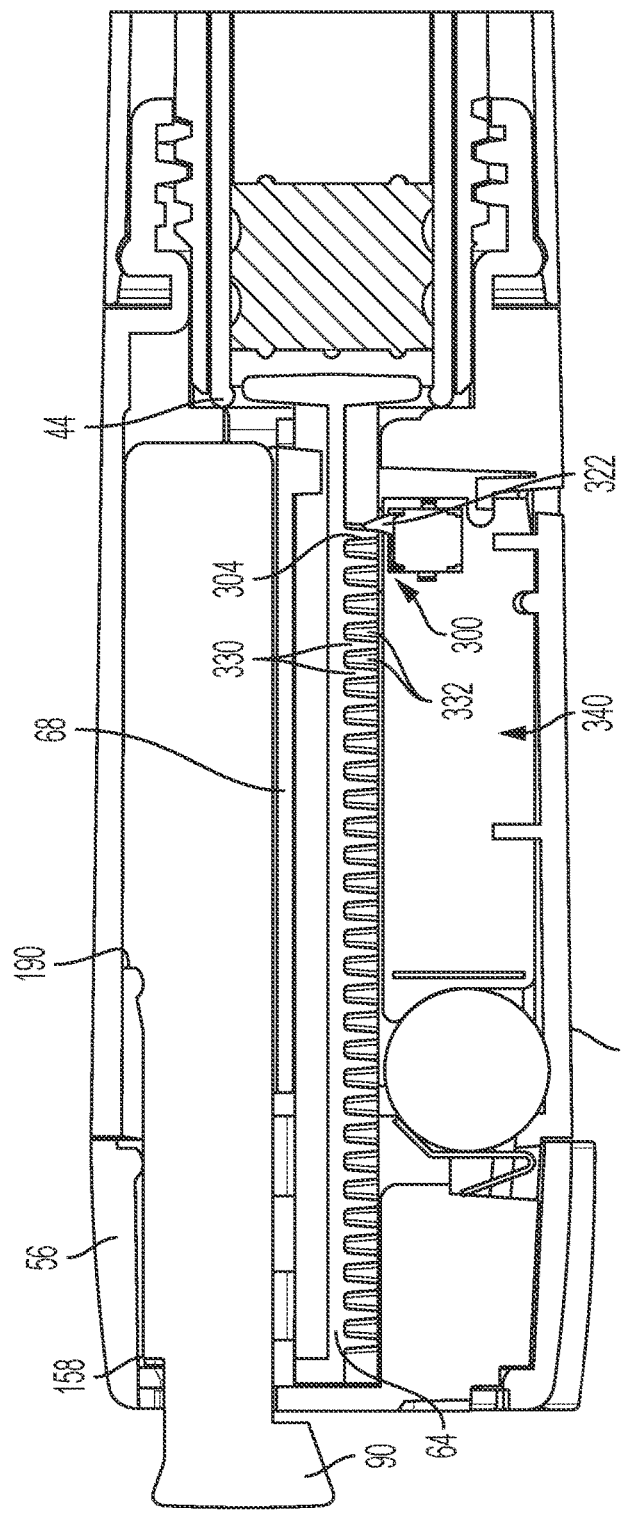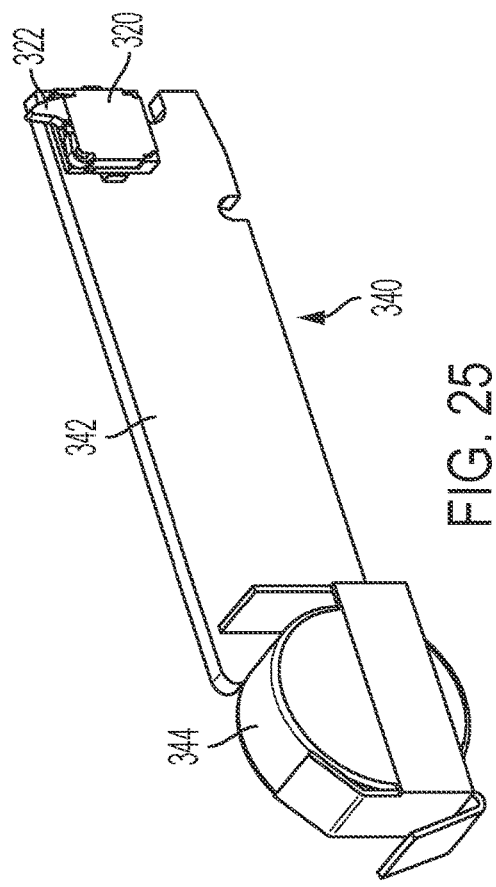

MEDICATION DELIVERY DEVICE WITH GEAR SET DOSAGE SYSTEM

CROSS-REFERENCE TO RELATED APPLICATION

The present application is a continuation of U.S. Patent No. 11,179,522 which is a National Stage application, filed under 35 U.S.C. s. 371, of International Patent Application No. PCT/US2020/023514, filed on Mar. 19, 2020, which claims the benefit of and priority to, under 35 U.S.C. § 119(e), U.S. Provisional Application Ser. No. 62/826,232, filed on Mar. 29, 2019, all which are hereby incorporated herein by reference in their entirety for all that it teaches and for all purposes.

BACKGROUND

The present disclosure pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

It would be desirable to provide a medication dispensing device with improved features, such as accommodating differently sized doses or a dose detection sensing system that can overcome one or more of these and other shortcomings of the prior art.

SUMMARY

A medication delivery device including a housing including one or more housing rack teeth, a plunger to drive a piston disposed within a medication cartridge barrel, the plunger body including a plurality of ratchet teeth; and a plunger drive system configured to distally advance the plunger. The plunger drive system includes an output drive member having one or more pawled ends movably coupled with the ratchet teeth of the plunger. At least one pinion drive is engaged with the drive teeth of the output drive member and the housing rack teeth of the housing. An actuator is coupled to the at least one pinion drive. In one embodiment, the actuator has a unitary piece body extending between a button end and the coupling end disposed within the housing. The actuator is longitudinally movable between an extended position for dose setting and a retracted position for dose delivery. In response to movement of the actuator to the extended position from the retracted position, rotation of the at least one pinion drive in a first direction along the drive teeth is configured to axially translate the output drive member relative to the plunger, with the one or more pawled ends of the output drive member sliding along the ratchet teeth of the plunger. In response to movement of the actuator to the retracted position from the extended position, rotation of the at least one pinion drive in a second direction along the drive teeth is configured to axially translate the output drive member, with the one or more pawled ends of the output drive member in engagement with the ratchet teeth of the plunger to prevent the output drive member from translating axially relative to the plunger, thereby advancing the plunger in a distal direction. In one embodiment, a dose selector may be included to allow variation of the dose set by the actuator. In one embodiment, a dose detection sensor system may be incorporated to detect, determine, display and/or communicate the detected dose to an external control system. In one embodiment, the actuator may also include a load brake system.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIGS. 5a-6a are each different perspective views of another example of a plunger.

FIGS. 10a-11a are each different perspective views of another example of an output drive element in a plunger drive system.

FIGS. 12-14 are each different perspective views of an example of an actuator in a plunger drive system.

FIGS. 15-16 are perspective views of each of the pinion drive elements, respectively.

FIGS. 15A-16A are perspective views of each of the pinion drive elements, respectively.

FIG. 24 is a cross-sectional view of a proximal portion of the delivery device in FIG. 1, depicting the arrangement of one example of a dose detection system.

FIG. 25 is a perspective view of one example of an electronics assembly of the dose detection system.

Figure 1:
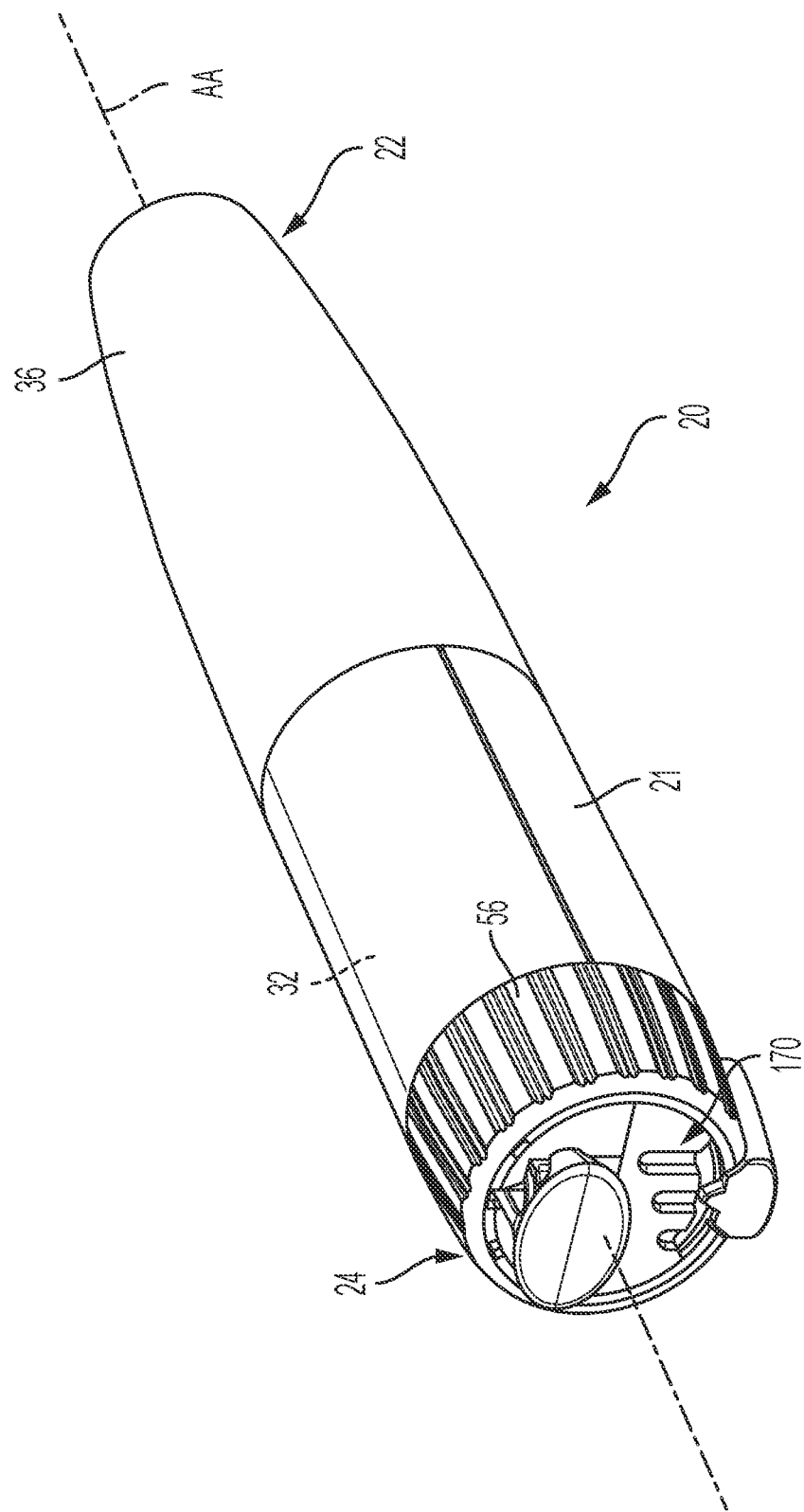
FIG. 1 is a perspective view of an example of a delivery device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

The shown device in FIG. 1 is an example of a pen-shaped medication injection device, generally designated 20, which is manually handled by a user to selectively set a dose and then to inject that set dose. In one example, device 20 may include a dose detection sensing system. The sensing system can be adapted for use in variously configured medication delivery devices, including differently constructed pen-shaped medication injection devices, differently shaped injection devices, and infusion devices. Any directional references in this detailed description with respect to FIG. 1 or any of the other Figures, such as right or left, up or down, or top or bottom, are intended for convenience of description, and by itself does not limit the present disclosure or any of its components to any particular positional or spatial orientation. When used, the term "distal" and "proximal" are used relative to the user and actuator button, and generally, during a patient's use of the device, the distal end, such as the needle end, would be closest in proximity to the patient, and the proximal end, opposite the distal end, would be farther in proximity from the patient.

Device 20 is shown including an elongated cylinder-like housing 21 disposed about a longitudinal axis AA, although other forms are within the scope of the disclosure. Device 20 may be disposable, in that after the quantity of medicine contained therein is exhausted by multiple operations of the device, the entire device is discarded rather than being reset and reloaded with a replacement container of medicine. Device 20 may be repeatably operable to deliver into a user a fixed dose, i.e., a dose in a specific amount that is dictated by the particular design of the device and that may not be changed without redesigning the device. Alternatively, device 20 may be configurable by a user, manufacturer, pharmacist, or health care provider to repeatably deliver one of multiple different dose sizes. In some embodiments, the device 20 may be configured to allow the manufacturer, pharmacist, or health care provider to set the dose size, but to prevent the user from modifying the dose size once set.

Device 20 generally includes a distal portion 22 and a proximal portion 24. Distal portion 22 contains the medicinal fluid to be outlet at its distal end upon pen operation. The outlet end of distal portion 22 is configured to receive an injection needle (not shown), when device is in an uncapped state. A cap 36 for the pen may be provided. Cap 36 may be sized to fit the device with or without a needle. Proximal portion 24 contains the injecting mechanism used to force the contained medicine from the needled end.

Figure 2:
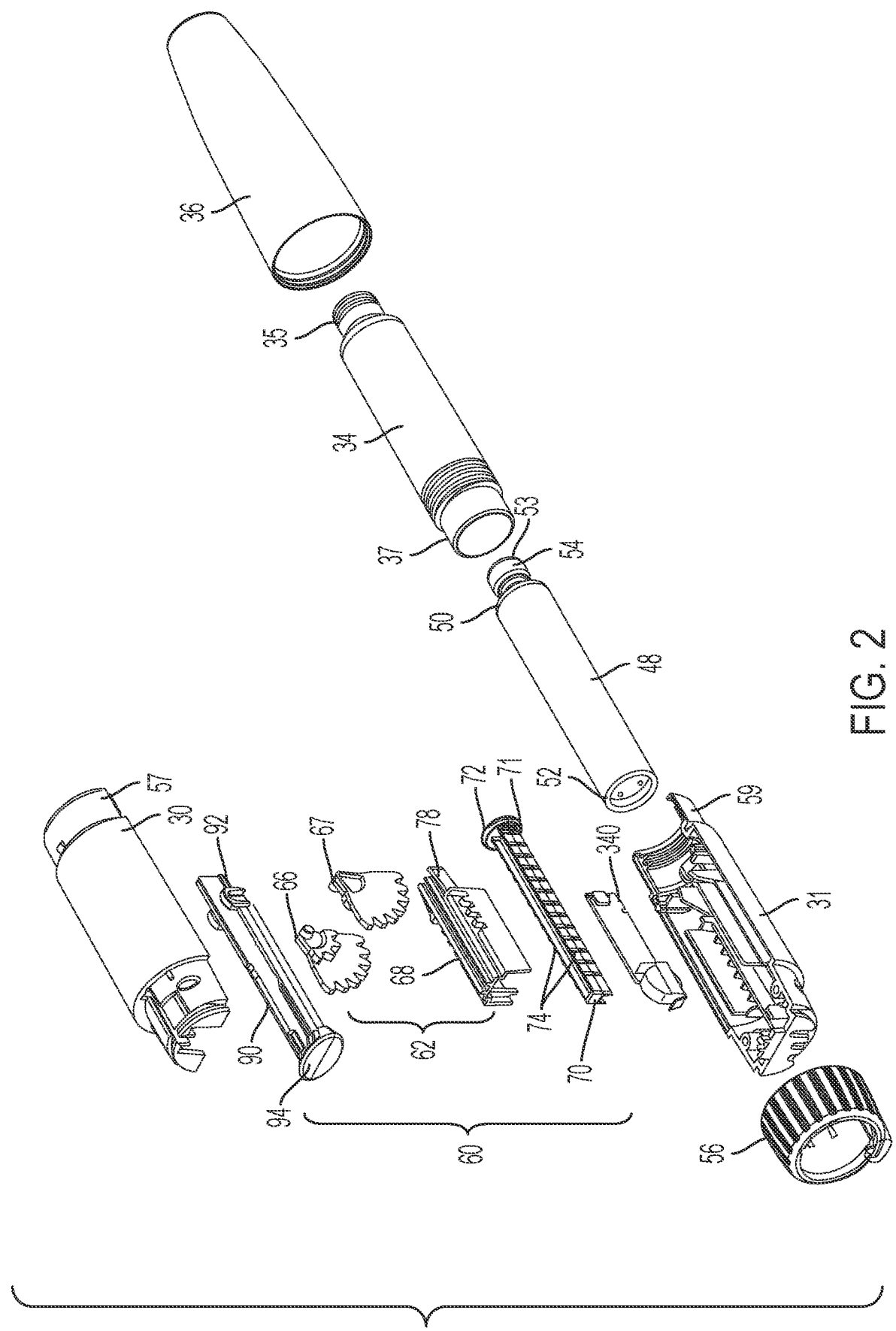
FIG. 2 is an exploded part perspective view of the delivery device in FIG. 1.
Figure 3:
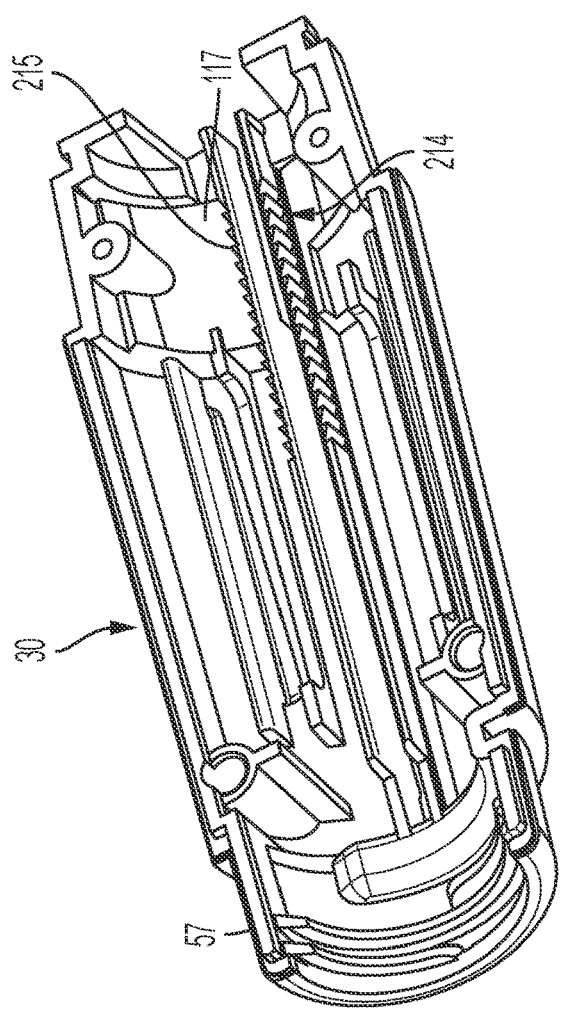
FIGS. 3-4 are perspective views of each of the device housing halves, respectively.
Figure 4:
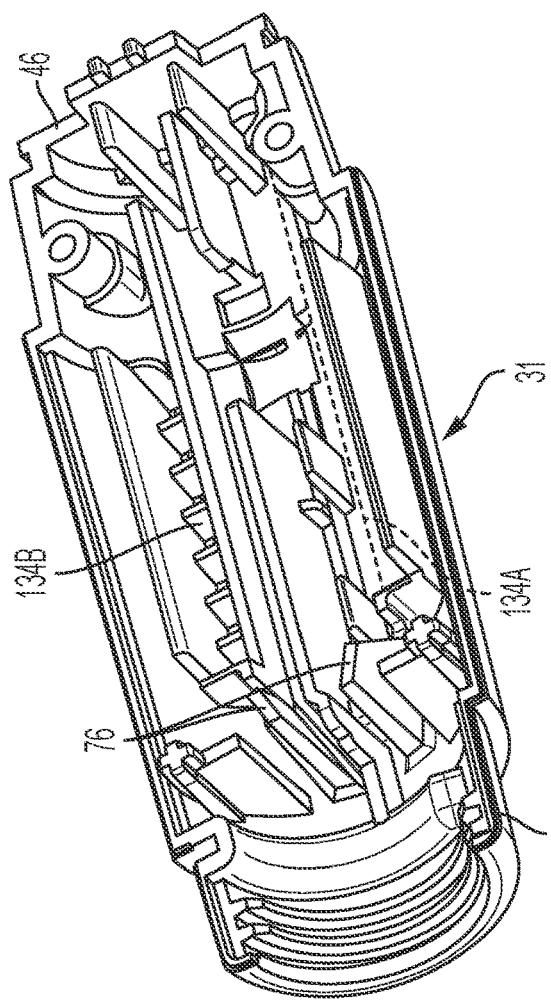

The device housing 21 may be formed from a lightweight material, such as injection molded plastic, in a single or multiple piece construction. Housing 21 is shown having two longitudinally extending halves 30 and 31, as shown in FIGS. 2-4. The housing halves 30 and 31 are aligned via mating pins and recesses provided therein and fixedly secured together during manufacture, such as via adhesives or ultrasonic welding. The device housing 21 defines an internal hollow 32 in which an axially advanceable plunger drive system, generally designated 60, extends at least generally along the longitudinal axis.

With additional reference to FIG. 2, distal portion 22 may include a tubular cartridge retainer 34 configured to hold a cartridge 48. The cartridge retainer 34 is shown as a discrete component that is coupled to the housing or may be formed in part as a distal extension of the housing 21. Retainer 34 may include a step-down distal end 35 configured for releasably coupling to the needle assembly. In one example, the retainer end 35 is configured for threaded engagement with the needle assembly. The proximal end 37 of the retainer 34 may define a cylindrical extension for coupling to the device housing 21.

The needle assembly (not shown) may include a double-ended needle cannula or injection needle having a distal tip at one end and a proximal point at the other. The injection needle includes a tubular hub that is configured for threaded engagement with retainer end 35 so as to be screwable onto and off of the threading of the retainer end. Other types of connection types, including a snap on connection, may be provided between the needle assembly and the cartridge retainer. The distal tip may be protected by a tubular shield coupled to the hub, as well as, a device cap 36 that is releasably attachable to, for example, the device housing 21, which the device cap 36 and/or shield is removed when device 20 is used to inject medicine. Needle assemblies which may be used with device 20 may include assemblies with one or more shortened injection needles.

Cartridge 48 defines a medicine-filled reservoir 50 that is closed at its proximal end by a piston 52 that is axially slidably and sealably engaged with the cartridge interior wall to hold the fluid medication within reservoir 50. The distal, outlet end 53 of cartridge reservoir 50 is sealed by a septum 54, shown generally at end 53. When the needle assembly is mounted to retainer end 35, the proximal point of the injection needle penetrates the cartridge septum 54 to provide a fluid flow path by which medicine within cartridge reservoir 50 can be dispensed from the needle tip during operation of device 20. Cartridge 48 is sandwiched between the interior surface of retainer 34, with its proximal end contacting an internal bulkhead 44 provided on housing halves 30 and 31, as shown in FIG. 24, to prevent axial movement of the cartridge during use. Other manners of capturing the cartridge relative to the housing may alternatively be employed.

Device 20 may further comprise a medication, such as in cartridge 48. In another embodiment, a system may comprise one or more devices including device 20 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

The interior surfaces of housing halves 30 and 31, respectively, are shown in FIGS. 3-4 formed with a variety of ribs and bulkheads that serve to maintain the alignment and guide the motion of the apparatus components disposed within housing 21. Housing halves 30 and 31 include distally projecting, curved flanges 57, 59, respectively. During manufacture, to mount the cartridge to the assembled housing, flanges 57, 59 are first coupled to the retainer proximal end 37, such as being inserted externally around or inside of the proximal end of retainer, and then fixedly secured to the retainer, such as via adhesives or ultrasonic welding. When retainer 34 and housing 21 are so secured, cartridge 48 is axially sandwiched. The proximal end of housing 21 defines at least partially a proximal end wall 46. The portion of the housing 21 adjacent the proximal end wall 46 may have a reduced cross-sectional area that is configured to receive a rotatable knob 56, as shown in FIGS. 2 and 24.

With reference to FIG. 2, and FIGS. 5-16, proximal portion 24 of device 20 includes the plunger drive system 60, which includes a gear set generally designated 62, a plunger member generally designated 64, an output drive element 68, and an actuator 90. Gear set 62 includes one or two pinion drive elements, shown as a pair 66, 67, and output drive element 68 that are operatively cooperative to distally advance the plunger member 64. The plunger, output drive element, and gear set components may each be injection molded in a single piece from a polymer or plastic material.

Figure 5:
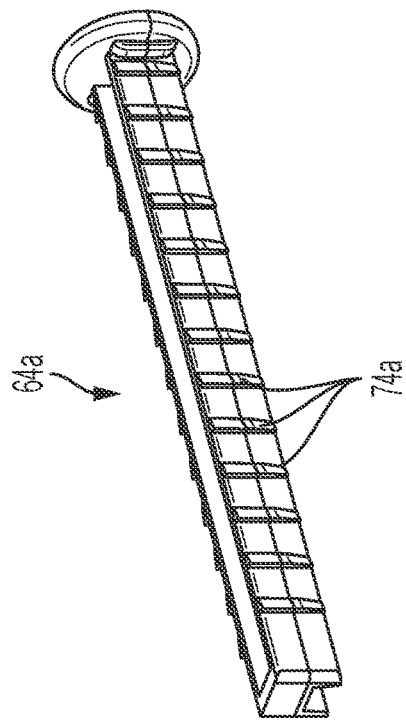
FIGS. 5-6 are each different perspective views of an example of a plunger.
Figure 6:
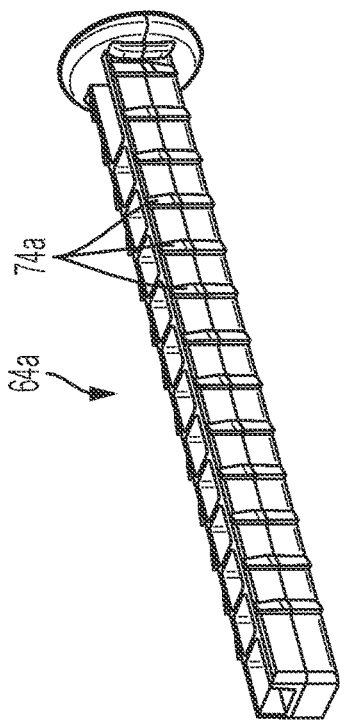
Figure 7:
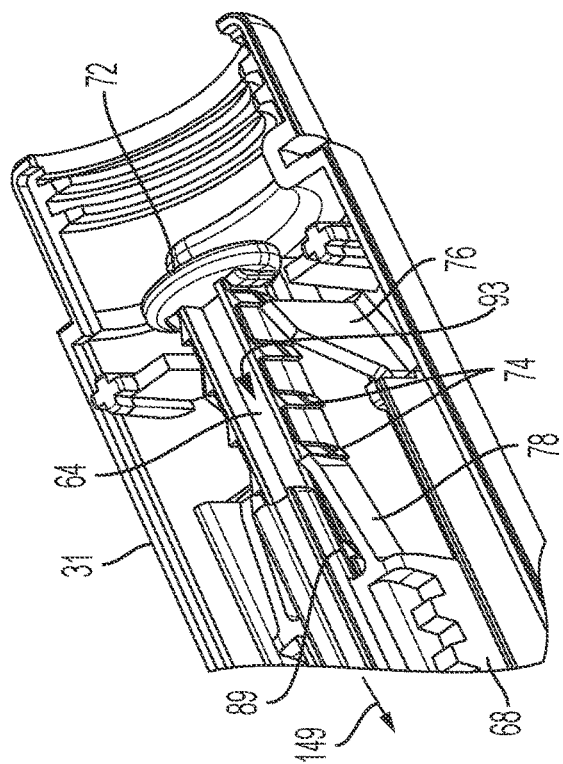
FIGS. 7-9 depict sequential operational steps of an example plunger drive system in the delivery device in FIG. 1.

With additional reference to FIGS. 5-7, plunger member 64 has a rectangular rod-shaped body that extends in the axial direction between a proximal end 70, and a load distributing, disc-shaped foot 72 formed at the distal end 71 of the body of the plunger member 64 to engage the piston 52. Foot 72 has a larger cross-sectional area than the transverse cross-sectional area of general body of the plunger member 64 to distribute loading on the cartridge piston 52 during piston advancing.

The drive member components are constrained by the internal shaping of housing halves 30 and 31 to be axially translatable therein. Plunger member 64 is movable in the distal direction and prevented from proximal movement relative to the housing 21, while output element 68 is clutchably connected to plunger member 64 to be moveable relative thereto in a proximal direction but not the distal direction. To provide for these one-way axial motions, ratchets are employed in the shown embodiment, but other elements may be used. For example, a hard but compliant toothed member or members, such as made of metal, may be provided in tight engagement with a smooth, such as cylindrical, and relatively soft member lacking surface features, which metal tooth/teeth are arranged such that motion of the other member in only a single direction is permitted, as in the opposite direction the tooth/teeth dig into and deform the relatively soft surface to create a wedging action that impedes further motion in that direction.

Figure 5A:
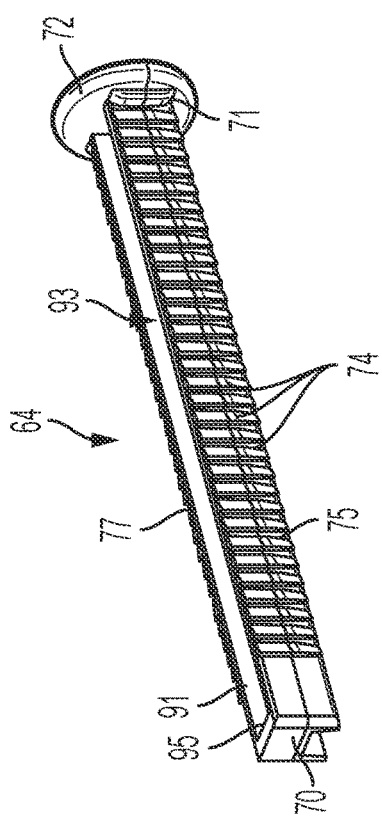
Figure 6A:
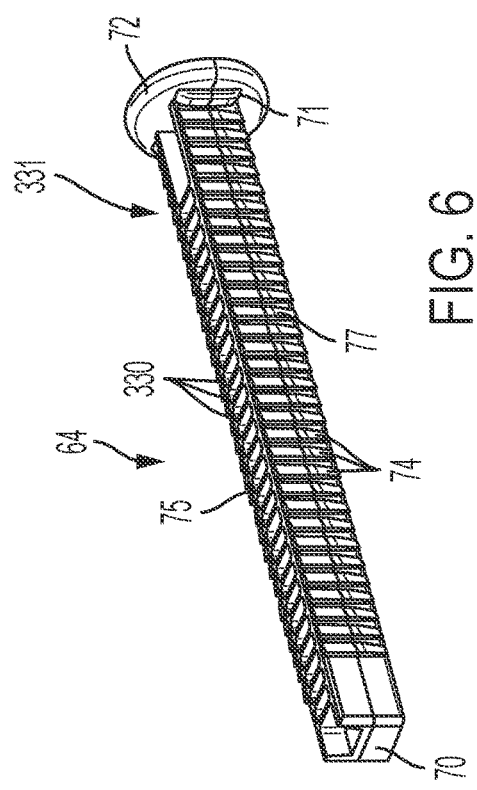

In one example, body of plunger member 64 includes a row of one-way ramping ratchet teeth 74 on two oppositely facing sides 75, 77 of its body, which teeth 74 continue uninterrupted along a portion of the axial length of the body. Other examples of a plunger may include a single side of ratchet teeth. The axial positioning and length that each row of teeth can span along its respective side is a function of various pawls' positioning and intended use, such as the total injection volume and number of discrete injections of device 20, as discussed in further detail below. Teeth 74 are axially spaced from one another to corresponding to a desired fixed dose per one or more teeth, which also correlates a dose per a number of clicks, such as a dose per a single click, a dose per 2 clicks, etc. FIGS. 5-6 illustrate relatively closer spacing of teeth 74 for the plunger member 64 configured for a smaller dose, such as, for example, 100 microliters-per-click. A click is generated during advancement of the plunger member 64 by one tooth 74 passed the fixed pawls 76. FIGS. 5A and-6A illustrate spacing between teeth 74a that is larger relative to teeth 74 for the plunger member 64a configured for a larger dose, such as, for example, 250 microliters-per-click. Plunger 64a is shown being capable of having all of the features of plunger 64. Ratchet teeth 74 are engaged by a pair of diametrically opposed, resilient housing tabs or pawls 76 (see FIG. 4) fixed and integrally formed with housing half 31. As further shown in FIGS. 7-9, pawls 76 slide along and over teeth 74 when plunger member 64 is advanced distally during use, but abut the transverse, proximal face of teeth 74 to prevent plunger member 64 from backing up in the proximal direction.

Figure 8:
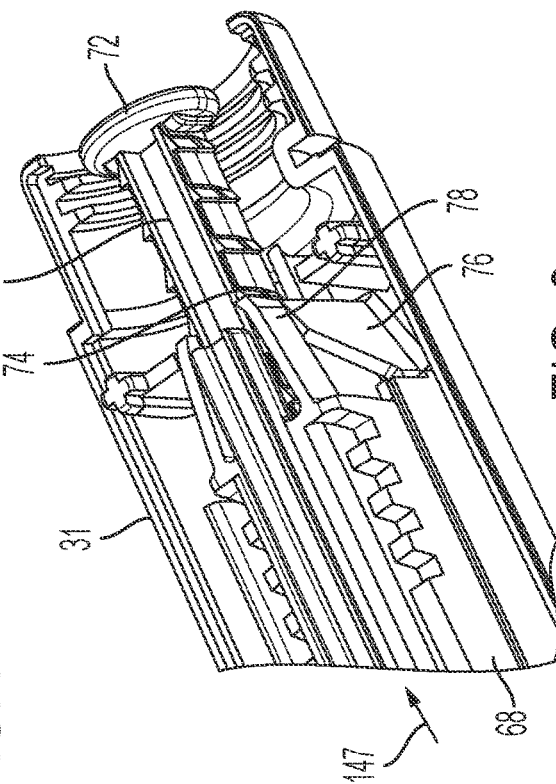
Figure 9:
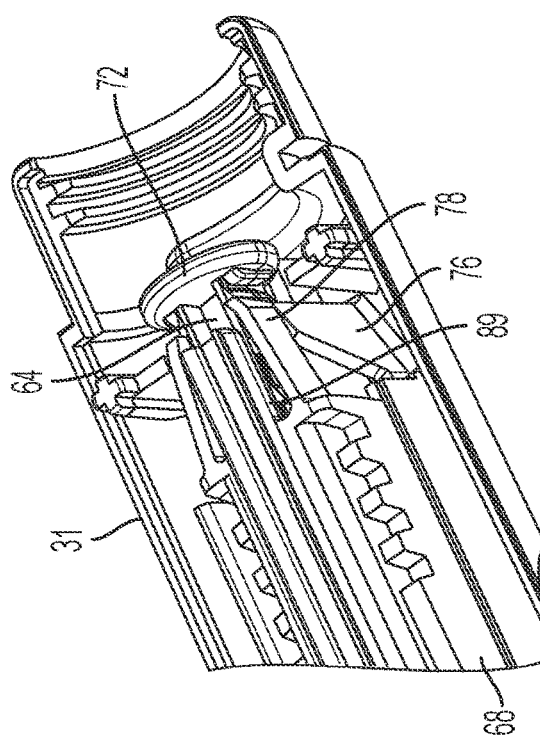
Figure 10A:
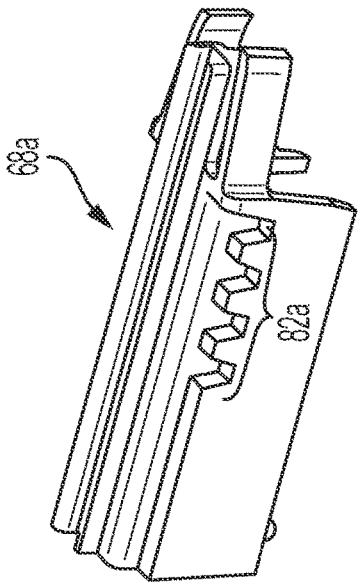
Figure 11A:
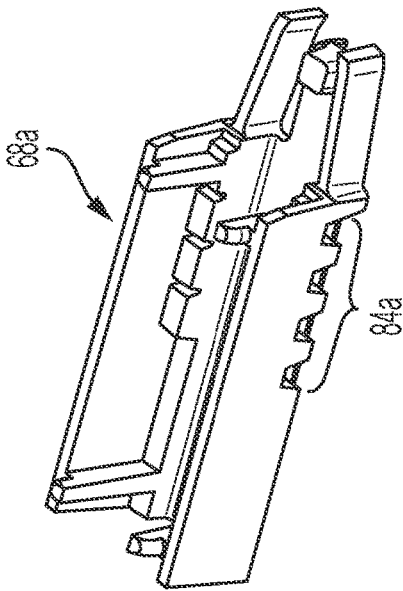
Figure 10:
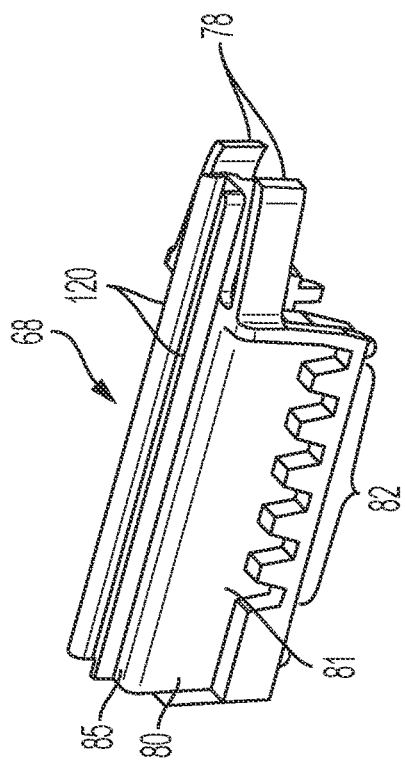
FIGS. 10-11 are each different perspective views of an example of an output drive element in a plunger drive system.
Figure 11:
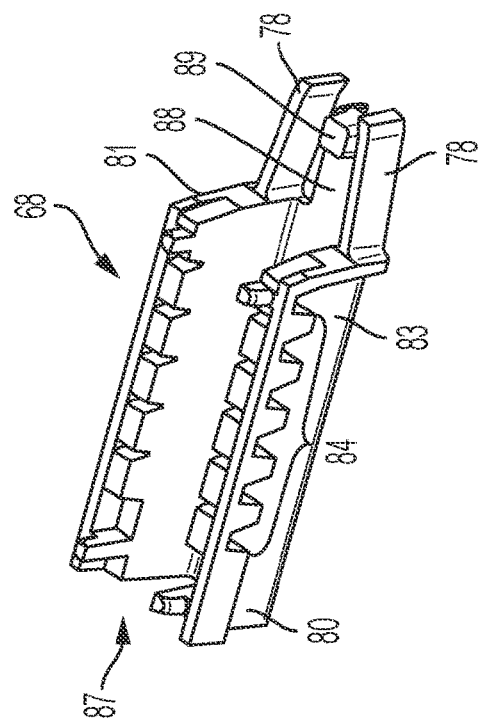

With additional reference to FIGS. 10-11, output drive element 68 includes a pair of diametrically-opposed resilient pawls 78, disposed proximal to the fixed housing pawls 76 when output drive element 68 is retracted proximally, to also engage the same rows of ratchet teeth 74 on opposite sides 75, 77 of body of plunger member 64. With reference to FIGS. 7-9, when drive element 68 is moved distally, the pawls 78 moves in the distal direction beyond the fixed housing pawls 76 to provide certainty that fixed pawls 76 have clicked over the ratchet teeth of the plunger member. As shown in FIG. 9. Pawls 78 and fixed pawls 76 are each disposed along a different surface portion of the ratchet tooth 74. For example, Pawls 78 engage an upper portion of the ratchet tooth, and fixed pawl 76 engage a lower portion of the ratchet teeth such that, when pawls 78 move past fixed pawls 76, the fixed pawls 78 are underneath the pawls 76. If the pawls 78 do not move past the fixed pawls 76, then the ratchet of plunger member 64 may back up the next time a dose is set, which may lead to an incorrect dose. To insure click-over occurs (i.e., to insure that fixed pawls 76 have clicked over the correct number of ratchet teeth 74 at the end of a dose), the end-of-travel position of pawls 78 is distal to the fixed position of pawls 76 by a distance called the "click-over margin." For a plunger with a single side of ratchet teeth described above, the output drive element may include a single pawl. Output pawls 78 slide along and over one or more teeth 74 when output drive element 68 is retracted proximally during device cocking, but in abutment engagement with at least one of teeth 74 during the distal advancement of output drive element 68 during injection. As the pawls 78 slide over the teeth 74, clicking sounds may be generated during dose setting. The abutting results in output drive element 68 shifting the plunger member 64 in the distal direction until end of travel. The pitch or distance between the transverse face of each adjacent tooth 74 may be the distance piston 52 needs to be advanced to deliver a fixed dose as predetermined by the manufacturer.

Output drive element 68 is shown having a U-shaped body 80 with a pair of longitudinally extending parallel, opposite facing sides 81, 83 interconnected by a third side 85, transversing the sides 81, 83, to define a plunger member receiving passage 87. A longitudinally extending first rack of teeth 82 projects from one side 81 of body 80, and a longitudinally extending second rack of teeth 84 projects from the opposite side 83 of body 80. The body 80 is sized to fit over the body of plunger member 64. To this end, when coupled, the body of plunger member 64 is received axially within passage 87 of the body 80 such that the sides 81, 83 are in a confronting, overlapping relationship with the teeth sides 75, 77 of the plunger member 64 and the third side 85 is in a confronting overlapping relationship with a non-toothed side 91 of the body of plunger member 64. The non-toothed side 91 may interconnect the sides 75, 77 of the plunger body. In this arrangement, the pawls 78 are now engageable with the teeth 74 of the plunger member 64. The pawls 78 may extend from the distal surface of the sides 81, 83.

A mechanical feature may be included to prevent operation of the device when there is insufficient remaining dose (IRD) within the cartridge 48 with an IRD arrangement. In the example shown, the third side 85 includes a distal extension 88 extending beyond the racks 82, 84. The distal extension 88 is shown disposed between the pawls 78. The distal extension 88 may include an IRD tab 89 extending from the interior surface of the distal extension 88 in the space defined between the pawls 78. The IRD tab 89 is configured to fit within an IRD slot 93 defined in the non-toothed side 91 of the member 64, with the IRD tab 89 and slot 93 defining the IRD arrangement. The IRD slot 93 extends between the foot 72 and the proximal end 70. A physical stop lip 95 is defined by the plunger member 64 toward the proximal end 70 and is configured to contact the IRD tab to physically prevent further movement of the output drive element, and thus further proximal withdrawal of the actuator 90 (discussed below) during dose setting, indicating that there is an insufficient remaining dose. FIGS. 10-11 illustrate the lower location and number of rack of teeth 82, 84 for the output drive element 68 configured for a smaller dose, such as, for example, 100 microliters-per-click, for use with the plunger member 68 shown in FIGS. 5-6. FIGS. 10A-11A illustrate the relatively upper location and fewer number of rack of teeth 82a, 84a for the output drive element 68a configured for a larger dose, such as, for example, 250 microliters-per-click, for use with the plunger member 68a shown in FIGS. 5A-6A. Output drive element 68a is shown being capable of having all of the features of output drive element 68a.

Actuator 90 extendable proximally beyond the housing 21 of device 20 is provided to allow a user to operate the internal gear set of the apparatus to prepare device 20 for injection, by withdrawing the actuator in the proximal direction from the device housing to an extended dose set configuration from a retracted configuration, as well as to perform the injection by pushing the actuator in the distal direction from the extended configuration to the retracted dose delivered configuration. In FIG. 2, actuator 90 includes an axially extending body extending between an input end 92 and a button end 94. Although not shown, a spring coupled between the actuator and the housing may be included for biasing the actuator towards a predefined position, such as the retracted position, and/or to dampen the movement of the actuator.

With reference to FIGS. 12-14, the button end 94 of actuator 90 includes an enlarged cross-sectional button 198, when compared to the remaining body, upon which the user applies an actuation input force. At the input end 92, the actuator includes a pinion-coupling feature configured to couple to the pinion drive elements. For example, the actuator 90 includes a first side 96 with a first pinion-coupling feature 100A, shown as slot 102 defined into the first side 96 with slot-defining walls that are sized and configured to receive a first laterally-extended pin 104 defined by the first pinion drive element 66. When the actuator 90 includes a second side 98, opposite of the first side 96, with a second pinion-coupling feature 100B, shown as slot 106 defined into the second side 98 with slot-defining walls that are sized and configured to receive a second laterally-extended pin 108 defined by the second pinion drive element 67. The pinion coupling feature between the actuator and the pinion drive element may include other configurations, such as the actuator including an upper internal slot to receive a pin rod extending between the confronting faces of both of the pinion drive elements, from the upper end or lower end, or a pin configuration to be received by slots defined in the pinion drive elements.

Figure 18:
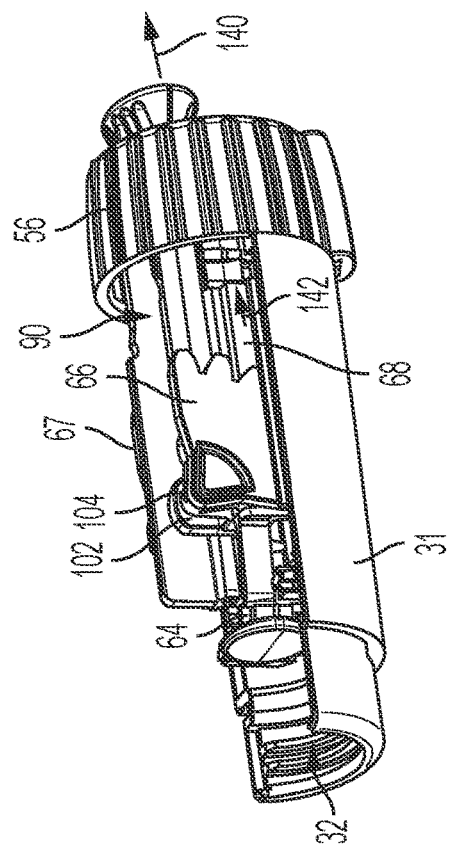
FIGS. 18-19 depict sequential operational steps of an example plunger drive system in the delivery device in FIG. 1.
Figure 19:
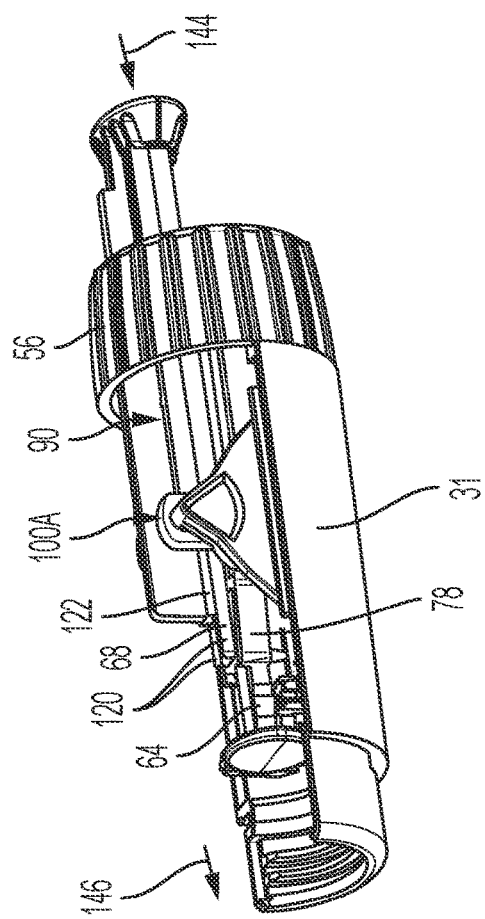

The actuator 90 may include a guide rail element 110 for interfacing with the housing and/or or components to control the axial movement of the actuator. Guide rail element 110 extends axially away from the button end 94, and may be disposed extending axially between the first and second sides 96, 98. The distal end 112 of the guide rail element 110 may extend distally beyond the distal ends of the first and second sides 96, 98, including extending distally beyond the slots 102, 106. The upper end 114 of the guide rail element 110 may extend radially beyond the walls defining the slots 102, 106 of the first and second sides 96, 98, respectively. Axially extending upper end 114 has a material thickness that is sized to fit within and be slidably disposed between a pair of axially extending parallel guide ribs 116 depending from an interior surface 117 of housing half 30 (see FIG. 3 and FIG. 23). The axially extending lower end 118, opposite the upper end 114, has a material thickness that is sized to fit within and be slidably disposed between a pair of axially extending parallel guide ribs 120 extending away from the third side 85 of output drive element 68 (see FIG. 10). A shelf 122 may extend laterally from one or both sides of the guide rail element 110. The shelf 122 may be disposed in between the upper end 114 and lower end 118 of the rail 110 at a desired distance to set the depth of the penetration of the shelf 122 into the space between the ribs 120 and to stabilize the sliding of actuator 90 along the upper surface of ribs 120, as shown in FIGS. 18-19. In other embodiments, it is the actuator that defines the guide ribs and a guide rail of the output member resides within the guide ribs. The guide rail element 110 may define the rigid portion of the actuator body.

The gear set 62 utilized in device 20 is configured to convert actuator motion of a first axial distance into drive member motion of a second axial distance less than the first distance. The first and second pinion drive elements 66, 67 of gear set 62 can be made from a lightweight material such as plastic. Each of pinion drive elements 66, 67 are coupled between the housing 21, such as, for example, housing half 31, the output drive element 68 and the actuator 90.

Pinion drive elements 66, 67 may be similarly configured. FIG. 15 depicts one side of pinion drive element 66 and FIG.

16 depicts one side of pinion drive element 67 from different perspectives, and for the opposite sides of the respective pinion drive elements 66, 67 that are hidden. In other words, FIG. 16 and FIG. 15 may be used to depict the hidden sides for pinion drive elements 66, 67, respectively. Pinion drive element 66 includes a first or larger sized pinion 130A that includes an arcuate section of external gear teeth 132A that mesh with teeth of a first rack 134A, shown located by dashed line in FIG. 4, defined by the housing half 31 of housing 21. Pinion drive elements 67 includes a first or larger sized pinion 130B that includes an arcuate section of external gear teeth 132B that mesh with teeth of a second rack 134B defined in the housing half 31 of housing 21. The teeth of racks 134A, 134B, respectively, are shown in FIG. 4, disposed from the interior surface of the housing half 31 spaced from one another in a parallel relationship. An arcuate section of gear teeth is all that is required due to the small angle of revolution, such as, for example, approximately 90 degrees plus or minus five degrees of revolution angle or roll, of the pinion necessary for use of the shown pen, which small angle or partial roll is possible due to the nominal range of 1.5:1 to 6:1 mechanical advantage provided by the shown gear ratio. Other gear ratios may be configured for desirable mechanical advantage less or greater than the above-referenced nominal range.

Pinion drive element 66 includes a second or smaller sized pinion 136A that includes an arcuate section of external gear teeth 138A that mesh with the teeth of second rack 84 of output drive element 68. Pinion drive element 67 includes a second or smaller sized pinion 136B that includes an arcuate section of external gear teeth 138B that mesh with the teeth of first rack 82 of output drive element 68. Each of the smaller sized pinions 136A, 136B has the same axis of rotation RA as the corresponding larger-sized pinions 130A, 130B of the respective pinion drive element. Gear teeth 138A, 138B may have a pitch diameter that is less than the pitch diameter of the corresponding gear teeth 132A, 132B. In the shown embodiment, such diameter is in a range of about 70 to 80% of the diameter of gear teeth, which ratio provides the nominally 4 to 6 to one mechanical advantage. Smaller ratios may be employed, such as down in the range of 40 to 50%, which realizes a 1.5 to two to one mechanical advantage, and larger ratios may alternatively be employed, such as realizing a ratio for a sixteen to one mechanical advantage. The size and/or number of teeth and racks of the housing, pinions and the output drive element provide a mechanical advantage structure that can vary its mechanical advantage depending on the relative sizes. Although each of pinion 130A, 130B and corresponding pinion 136A, 136B can be integrally formed, these components can be separately formed and assembled together. Pin 104 or 108 is located at such axis RA and is shown integrally formed with the pinions. Each of pins 104, 108 is sized and shaped to fit into, and pivot or partially rotate within, the respective slot 102, 106 defined in actuator 90 during use. In other embodiments, the coupling between the pinion drive elements and the output drive element is not a rack/pinion arrangement. For example, each of the pinion drive elements may include a pin inserted within corresponding slots defined in the outer sides of the output drive element. In another example, each of the pinion drive elements may include one or more cammed surfaces for rolling engagement with corresponding one or more pins extending outward from the sides of the output drive element. In another example, each of the pinion drive elements may include a protruding non circular tooth inserted within corresponding slot defined by the sides of the output drive element. In another example, each of the pinion drive elements may define a slot for receiving corresponding oblong tooth extending outward from the sides of the output drive element. FIGS. 15-16 illustrate the lower radial location (farther from radial axis RA) and higher number of pinion teeth 138A, 138B for the pinions 66, 67, respectively, configured for a smaller dose, such as, for example, 100 microliters-per-click, for use with the output drive element 68 and plunger member 64. FIGS. 15A-16A illustrate the relatively upper radial location (closer in proximity to the radial axis RA) and fewer number of pinion teeth 138A', 138B' for pinions 66A, 67A, respectively, configured for a larger dose, such as, for example, 250 microliters-per-click, for use with the output drive element 68a and plunger member 64a. Pinions 66A, 67A are shown being capable of having all of the features of pinions 66, 67.

Figure 17:
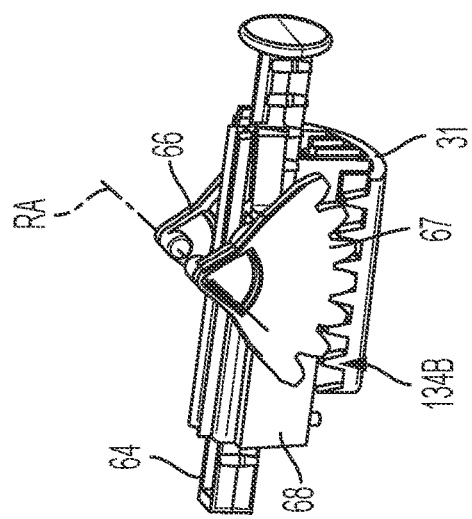
FIG. 17 is a perspective view of an assembly of the pinion drive elements, the output drive element, and the plunger in a plunger drive system.

FIG. 17 illustrates the rolling interaction of the larger sized pinion of pinion drive elements 66, 67 with the fixed racks (rack 134B shown) of the housing half 31, and the rolling interaction of the smaller sized pinion of pinion drive elements 66, 67 with the respective racks 82, 84 or 82a, 84a of output drive element 68 or 68a, that are obstructed from view by the pinions, to advance the plunger member 64.

FIGS. 18-19, as well as FIGS. 7-9, illustrate the operation of the device 20, with some components omitted to bring clarity to the internals of the device. For example, the device shown in FIG. 18 is with actuator 90 in its retracted position, which in this position the device is ready to be set or the dose has been delivered. FIG. 7 illustrates the position of the distal end of the output drive element 68 in relation to the plunger member 64 when the actuator is in its retracted position. When a lock is employed, such as, for example, with the knob 56, to prevent inadvertent dose setting of the actuator, the user will unlock the device. The user applies a force in the proximal direction (shown by arrow 140) to the actuator 90 to withdraw the actuator from its retracted position to allow positioning of pinion drive elements 66, 67 of the gear set 62 and thus the rack and pinion coupling of the output drive element 68 to move element 68, as depicted by arrow 142, axially in the proximal direction over the plunger member 64 that remains stationary. FIG. 8 illustrates the position of the distal end of the output drive element 68 in relation to the plunger member 64 when the actuator is being withdrawn in the proximal direction show by the arrow 149 from its retracted position. The housing pawls 76 are in abutment engagement with the ratchet teeth 74 to prevent the plunger member 64 from moving in the proximal direction, while element 68 is in movement. This relative movement between output drive element 68 and plunger member 64 is enabled by the ability of the pawls 78 on output element 68 to slidably move over the ratchet teeth 74 of the plunger member 64 in the proximal direction. The device shown in FIG. 19 is with actuator 90 in its extended dose set configuration, which in this position the actuator has been withdrawn to perform the injection. The user applies a force in the distal direction (shown by arrow 144) against the actuator 90 to push the actuator to its retracted position to allow actuation of pinion drive elements 66, 67 of the gear set 62 and thus the rack and pinion coupling of the output drive element 68 to advance element 68 together with the plunger member 64 in the distal direction, as shown by arrow 146. This movement is from engagement of the pawls 78 against the ratchet teeth 74 that prevents the plunger member 64 from moving axially in the proximal direction relative to the output drive element 68. FIG. 9 illustrates the position of the distal end of the output drive element 68 in relation to the plunger member 64 when the actuator is pushed all the way in in the distal direction shown by the arrow 147 from its extended position to distally advance the plunger member for dose delivery.

Figure 20:
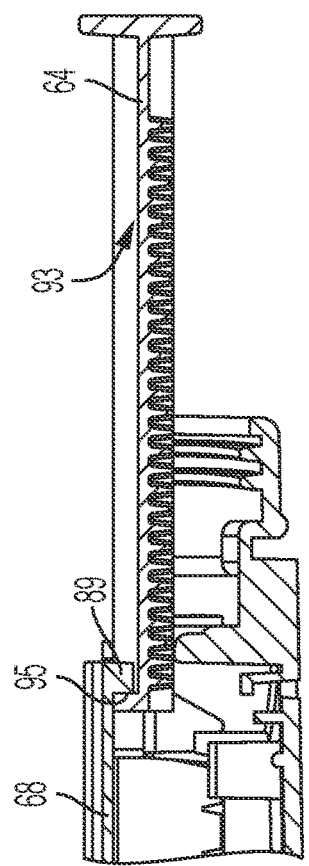
FIG. 20 depicts operation of the device components when there is insufficient remaining dose left in the delivery device.

FIG. 20 illustrates that the devices described herein may be prevented from complete operation when there is insufficient remaining dose by inhibiting the actuator 90 from being withdrawn. The output drive element 68 is shown being unable to move any further in the proximal direction relative to the plunger 64 by the IRD tab 89 that is slidably disposed within the IRD slot 93 by engaging the stop lip 95 of the plunger member 64 to set the IRD arrangement, as shown in FIG. 20. Prior to reaching the stop position, the output drive element 68 is able to move relative to the plunger member 64 as the IRD tab 89 slidably moves within the IRD slot 93 as shown in FIG. 9. The IRD arrangement may set during dose setting to inhibit the user from achieving the desired dose. For example, the IRD arrangement will prevent the dose setting of a desired dose units associated with 2 clicks, with the setting of the IRD arrangement after a single click, falling one click short of the desired dose. To this end, the user may need another device for delivery of the remaining dose.

Figure 22:
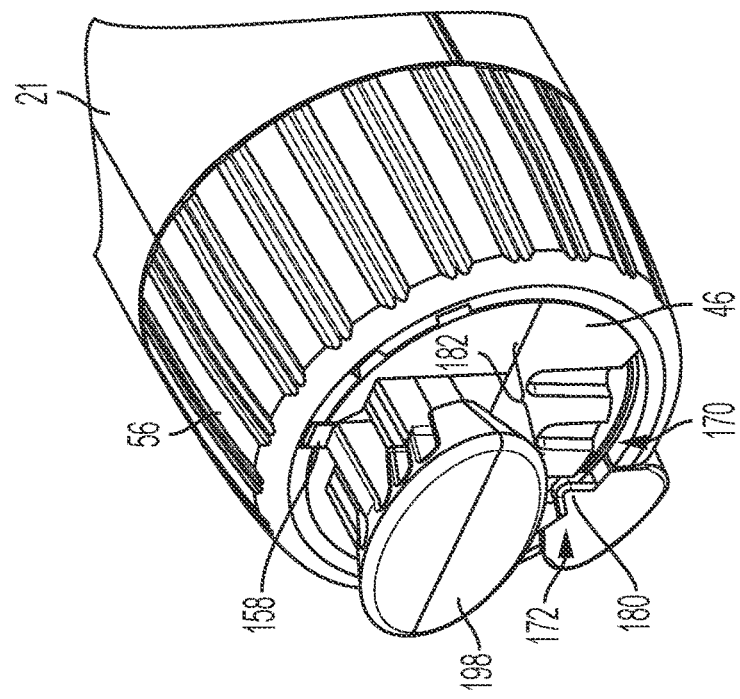
FIG. 22 is a perspective view of a proximal end of the delivery device in FIG. 1.
Figure 21:
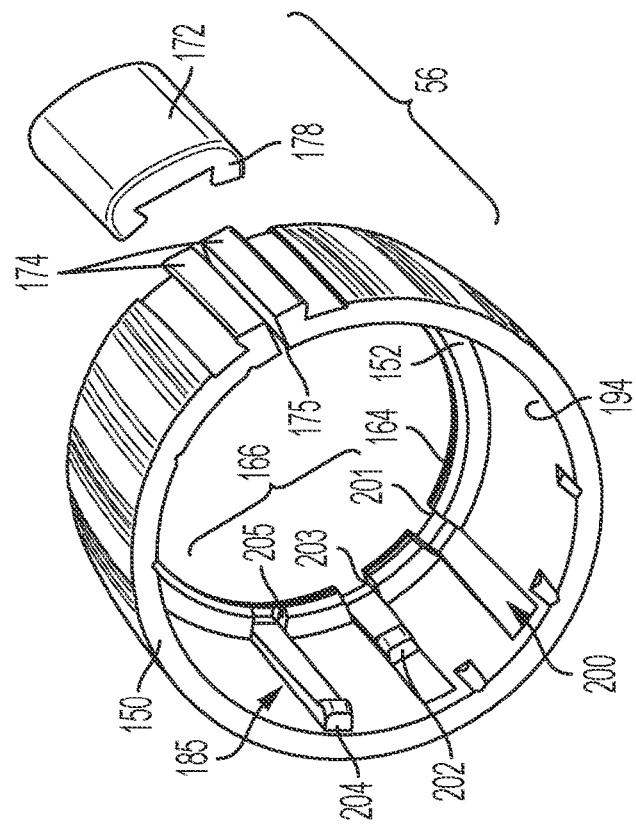
FIG. 21 is an exploded part perspective view of a dose knob with a dose selector feature.

In FIGS. 21-22, knob 56 includes a cylindrical body 150 sized to fit surrounding the proximal end of housing 21. The knob 56 may include an internal radial lip 152 for engagement with the housing end once the end of housing 21 is inserted within the knob body 150 during assembly. The knob 56 may be rotated to a lock position, shown in FIG. 18. Other configurations to lock the actuator may be utilized. Knob 56, when in its locked position, prevents the actuator 90 from being moved for dose setting. Only when rotated to an unlocked position, shown in FIG. 19, can the user withdraw the actuator 90 to set the dose. In one example, with additional reference to FIG. 12, the actuator 90 includes an interlock stop protrusion 158 disposed along the upper end 114 of the rail 110 of the actuator 90. The interlock stop protrusion 158 may be defined as a stepped region 160 of the rail 110, where the elevation of the interlock stop protrusion and stepped region 160 is above an adjacent recessed region 162 that is proximal to the interlock stop protrusion 158. At its locked position, a region 164 of the internal lip 152 of knob 56 is positioned across the travel path of the interlock stop protrusion 158, physically blocking the actuator 90 from farther proximal travel. At its unlocked position, a slotted region, shown generally as 166, of the internal lip 152 is positioned across the travel path of the interlock stop protrusion 158 to permit the actuator 90 to proximally travel for dose setting. The slotted region 166 is sized to receive and allow the passage of the interlock stop protrusion 158 and stepped region 160 therethrough.

One aspect of the devices described herein is their ability to deliver a fixed volume of dose a single time, if so configured, or a fixed volume of dose repeatedly multiple times. In one embodiment of the device, it may be desirable for a user or health care provide to vary the volume of the fixed dose during treatment, such as, for example, during a titration routine. To this end, the device 20 may include a dose selector 170 that is configured to limit the travel of the actuator 90 during dose setting to a position less than full travel corresponding to 100% of the fixed dose volume for a single injection. The dose selector 170 may be movable between at least two positions or more than two positions when the device is configured for more than two settings. When the dose selector 170 is in a first position, the actuator 90 is allowed to travel the full distance to permit a fixed dose volume of 100%. When the dose selector 170 is in a second position, the actuator 90 is allowed to travel less than the distance to permit delivery of a fixed dose volume of something less than 100%. The dose selector 170 may be included in any part of the device. In one example, the dose selector 170 in at least one of its positions engages the actuator 90 to inhibit the travel of the actuator to its 100% dose position. In one example, the dose selector 170 includes a portion that is contactable by the user so that the user can apply a force to the dose selector to shift to another position. In one example, the device 20 may include a dose indicator 172 to indicate to the user which dose is being selected by the dose selector and/or to indicate the locked position.

The knob body 150 and the indicator 172 may be integrally formed into a single piece. In FIG. 21, the knob body 150 may have a clam shell design to facilitate assembly to the device housing. The indicator 172 may be a separate piece that couples to the body 150. For example, the knob body 150 is shown with a pair of external coupling axial lips 174 disposed along the slot 175 of the knob body 150, and the indicator 172 has a body 178 to fit over the lips 174 in an interference fit. As shown in FIG. 22, the proximal end of the indicator 178 may include a pointer element 180 that overlaps the proximal end wall 46 of the device housing 21. The proximal end wall 46 may have markings, debossments, embossments, stickers, or other indications, shown generally as 182, to which the pointer element 180 is associated with to indicate the size of the fixed dose when the knob 56 is rotated.

FIG. 21-22 illustrates one example of the dose selector 170 of the device. Here, the dose selector 170 is defined by the knob 56 that includes slotted regions and/or one or more axial tangs. When more than one tangs 185 are provided, the tangs 185 are circumferentially disposed relative to one another. Each of the tangs 185 may extend in the distal direction at different axial lengths. Each of the tangs 185 are controllably positioned upon rotation of the knob 56 to engage a bump protrusion 190 disposed along the upper end 114 of the rail 110 of the actuator 90, which is shown in FIG. 12. The bump protrusion 190 is disposed distal to the interlock stop protrusion 158. The bump protrusion 190 may be defined as a second stepped region 192 of the rail, where the elevation of second stepped region 192 is above the adjacent stepped region 160 that is proximal to the bump protrusion 190.

In one example, the tangs 185 are disposed along the interior surface 194 of the knob body. FIG. 21 shows a slotted or tangless region 200, a first tang 202, and a second tang 204 longer than the first tang 202, each disposed circumferentially relative to one another along the interior surface 194 to define three dose setting positions. The tangless region 200 leads to a first slotted region 201 of the radial lip 152 to permit the actuator 90 to be withdrawn proximally for a full 100% fixed dose setting or large dose setting. Without a tang, the bump protrusion 190 travels up to the first slotted region 201 to engage the corresponding section of the radial lip 152. The first tang 202 leads to a second slotted region 203 of the radial lip 152 to permit the actuator 90 to be withdrawn proximally to a position less than the full position for full 100% fixed dose setting or a medium dose setting. The second tang 204 leads to a third slotted region 205 of the radial lip 152 to permit the actuator 90 to be withdrawn proximally to a position less than the full position for full 100% fixed dose and less than said position for the dose setting allowed by the first tang or a small dose setting. With the first and second tangs 202, 204, the bump protrusion 190 engages the respective tangs during withdrawal of the actuator to less than full travel to inhibit full travel through the respective slotted regions. In another embodiment, the tangs may be integral with a stepped tang that when positioned accordingly provides the varying dosages.

The length and number of axial tangs may be selected and modified to accommodate different variable fixed doses. In one embodiment, the length of the tang corresponds to a number of ratchet teeth. In other embodiments, the tangs 202, 204 may extend beyond the knob body. For example, the dose selector may be positioned for 100% fixed dose, 66% fixed dose and 33% fixed dose. Other percentages may be provided. In one embodiment, the large dose setting allows for three ratchet teeth distance travel, the medium dose setting allows for two ratchet teeth distance travel, the small dose setting allows for a single ratchet teeth distance travel. To this end, the axial length of the first tang is sized to reduce the 100% dose by one ratchet tooth, and the axial length of the second tang is sized to reduce the 100% dose by two ratchet teeth.

Figure 23:
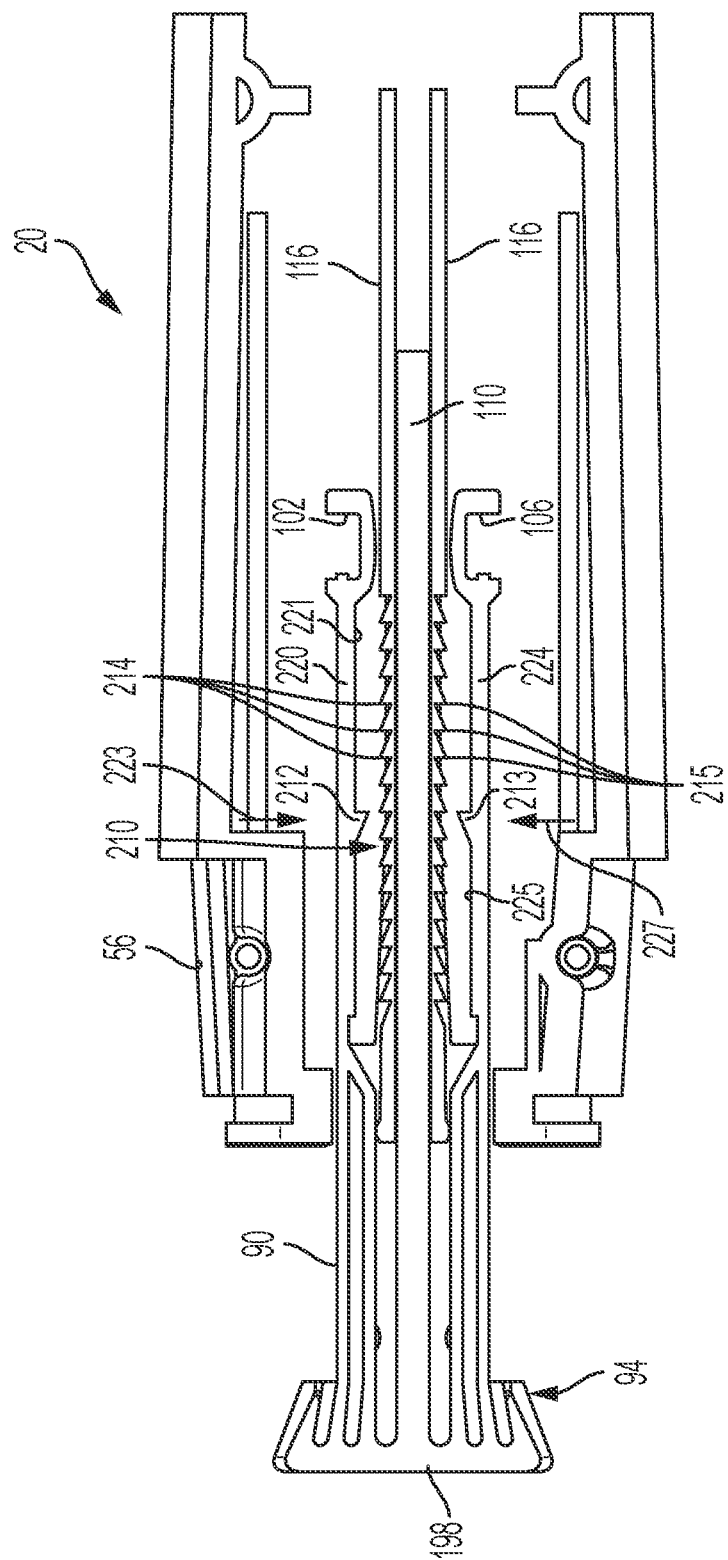
FIG. 23 is a cross-sectional view of a proximal end of the delivery device in FIG. 1.

FIG. 23 illustrates an example of providing a load brake system 210 to the device 20 to inhibit high loads applied to the actuator 90 from transferring into the gear set 62 and the plunger member 64 during dose delivery that could damage the components of the device. The actuator 90 may include a brake pawl 212 having at least one tooth that is engageable with a brake element 214 fixedly disposed in the housing 21 to define load brake system 210. The actuator 90 is shown including a first flex member 220, defining first side 96, and a second flex member 224, defining second side 98, extending axially from the button end 94. The first and second flex members 220, 224 are disposed on opposite sides of and in parallel spaced relationship with the rigid guide rail element 110. The flex member 220 includes the brake pawl 212 that is disposed along the radial interior surface 221 of the member 220 that faces the guide rail element 110. The flex member 224 includes the brake pawl 213 that is disposed along the radial interior surface 225 of the member 224 that faces the guide rail element 110. With additional reference to FIG. 3, brake element 214 is shown as a plurality of ratchet brake teeth disposed longitudinally along the exterior surface of one of ribs 116 of housing half 30. Housing 21 may also include axially extending ratchet brake teeth 215, shown disposed along the exterior surface of the other of ribs 116 of housing halve 30, for engagement with the brake pawl 213. The brake pawl may be disposed between the pin-coupling end and the button end 94.

The load force required to drive the piston within the cartridge to expel medication from the needle can be attributed to the various factors of the device, such as the size of the needle cannula, the size of the piston, the viscosity of the medication, the lubricant of the syringe barrel, frictional losses of the drive mechanism, and the like. The initial force to overcome the piston at static is greater than the force to continue to move the piston during dynamic movement. Devices can be designed with a predetermined load actuator force requirement during static and dynamic movement of the piston to inhibit excessive forces that can cause damage to internal components. The body of each of flex members 220, 224 of actuator 90 is configured to buckle, flexing radially inward from its natural configuration, at a predefined axial force provided by the user to the actuator 90. Such a load larger than this predefined axial force generates a moment (torque) on the flex members that causes them to flex. The radial flexing of flex members 220, 224 (in the direction of arrows 223, 227 in FIG. 23) places the respective brake pawls 212, 213 in engagement with one of the backside of the teeth of the corresponding ratchet brake teeth 214, 215 to inhibit any further movement of the actuator 90 relative to the housing. Once the force is reduced, the flex members 220, 224 may have a resiliency to return to its natural configuration (shown in FIG. 23), where the respective brake pawls 212, 213 are disengaged with and clear the teeth of the corresponding ratchet brake teeth 214, 215 to allow further advancement of the actuator. In other embodiments, a single flex member may be used instead of a pair. In other embodiments, the flex member may be configured to flex outward or upward to engage the ratchet teeth that can be disposed outward relative to the actuator. When the load is less than the predefined axial force, that is normal load forces, there is no flexing of the flex members to the degree of engagement and thus the load brake system may not provide additional frictional losses to the drive system under normal loads.

The actuator 90, with or without the flex members 220, 224, may be a unitary piece from the input coupling end to the button end, which may avoid the assembling of multiple components and use of a spring for actuation load dampening. In another example, the actuator 90, with or without the flex members 220, 224, may be manufactured by assembling several components like the flex members 220, 224 in a secured manner to form the unitary piece. In one example, the actuator 90 with the flex members 220, 224 and one or more of other features described herein is a moldable unitary part, such as, for example, from an injection molded plastic process. The actuator 90 with the flex members 220, 224 may be referred to as a springless actuator, since the load brake function occurs without a helical spring arrangement with the actuator.

FIG. 24 depicts the inclusion of a dose detection system 300 within the device 20, such that the device 20 can be configured to detect, indicate, display and/or communicate dose injection data to an external device, such as a smartphone or a server. Dose detection systems described herein use a sensing component 302 and a sensed component 304 coupled to members of the medication delivery device. The sensing component 302 may be attached to a member of the device 20 by being directly positioned on, received within, integral with, or otherwise connected to, the member. Connections may include, for example, connections formed by frictional engagement, splines, a snap or press fit, sonic welding or adhesive.

Sensing component 302 refers to any component which is able to detect the relative position of the sensed component 304. The sensing component 302 includes a sensing element, or "sensor", along with associated electrical components to operate the sensing element. Sensed component 304 refers to any component for which the sensing component 302 is able to detect the position and/or movement of the sensed component 304 relative to the sensing component 302. For the dose delivery detection system, the sensed component axially translates relative to the sensing component, which is able to detect the longitudinal position and/or the longitudinal movement of the sensed component, and to provide outputs representative of the position(s) or movement(s) of the sensed component(s). For the dose type detection system 300, the sensing component 302 detects the relative longitudinal position of the sensed component 304. The sensing component 302 may include one or more sensing elements, and the sensed component 304 may comprise one or more sensed elements.

The system 300 is operable to determine different longitudinal positions of the sensed component and/or total distance of travel. The sensing component 302 produces outputs representative of the position(s) or the amount of movement of the sensed component 304. For example, the sensing component 302 may be operable to generate outputs by which the distance travel of the dose setting member during dose delivery can be determined. System 300 may comprise a processing circuit (not shown) operably connected to the sensing component 302 to receive the outputs. In one aspect, system 300 is configured to determine from the outputs the amount of dose delivered by operation of the medication delivery device.

With the extent of longitudinal distance having a known relationship to the amount of a delivered dose, the system 300 is operable to detect the amount of longitudinal movement from the start of a dose injection to the end of the dose injection. For example, a typical relationship for a pen injector is that a longitudinal displacement of a plunger is the equivalent of a predetermined amount of units of dose, such as, 1, 2, 3, 4, 5, 6, or more, using any incremental units. The system 300 is operable to determine the total longitudinal displacement of a dose setting member during dose delivery in order for such data to be used to determine the dose delivered. An alternative approach is to detect the start and stop positions of the relatively moving member, and to determine the amount of delivered dose as the difference between those positions. Various methods for this are well within the ordinary skill in the art and may include "counting" the number of increments, that is ratchet teeth, to assess the distance travel and thus number of units delivered.

Any of a variety of sensing technologies may be incorporated by which the relative positions of two members can be detected. Such technologies may include, for example, technologies based on tactile, vibration, optical, inductive, capacitive or electrical measurements. Such technologies may include the measurement of a sensed parameter associated with a field, such as a magnetic field. In some embodiments, the movement and/or position of the sensed element in the sensed area relative to the sensing element changes a detectable parameter of the field, and this change in the detectable parameter may be sensed or measured by the sensing element. In such embodiments the sensed parameter may be a capacitance, conductance, resistance, impedance, voltage, inductance, etc. For example, Hall Effect sensors detect changes in voltage resulting from distortions of an applied magnetic field.

In the example shown, the sensing component 302 is mounted to a part of the device housing 21 and the sensed component 304 is defined in a component of the dose setting member shown as the plunger member 64. The sensed component 304 may also comprise the dose setting member, such as the actuator. The system 300 detects during dose delivery the relative longitudinal movement of the sensed component 304, and therefore of the plunger member 64, from which is determined the amount of a dose delivered by the medication delivery device. In an illustrative embodiment, the sensing component 302 is attached in a rotationally and longitudinally fixed manner to the device housing 21. In this embodiment, the sensed component 304 is rotationally and longitudinally fixed to the dose setting member that is the plunger member 64, which longitudinally moves relative to the device body during dose delivery.

Sensing component 302 is shown including an electromechanical switch 320 having a trigger arm 322 movable between two or more positions to generate an electrical output signal to be sent to the processor of a microcontroller. Sensed component 304 includes a series of sensed teeth 330 coupled to the dose setting member. In one example, sensed teeth 330 may be defined along a side 331 of the plunger member 64, as shown in FIG. 6. Side 331 may be opposite the non-toothed side 91 of the plunger body. The sensed teeth 330 can be integrally defined within the body side 331 of the plunger member 64. The sensed teeth 330 are shown longitudinally displaced from one another, spaced from one another by gaps 332. Gaps 332 are sized to receive at least a portion of the trigger arm 322. The trigger arm 322 may be triggered to a sensing contact position by movement of the sensed teeth 330 against the trigger arm 322, and, once a sensed tooth passes beyond the trigger arm 322, the trigger arm 322 is biased to return to a natural, resting position. One movement of the trigger arm 322 to its sensing contact position and then back to its natural resting position may be recognized by the processor of the microcontroller as a single count. Dose detection is achieved by counting increments (or total number of sensed teeth triggering the switch) to determine a delivered dose amount. In one example, the system 300 may use a repeating pattern of sensed elements, such that each repetition is an indication of a predetermined degree of longitudinal displacement. Conveniently, the pattern may be established such that each repetition corresponds to the minimum increment of dose that can be set with the medication delivery device. An alternative approach is to detect the start and stop positions of the relatively moving member, and to determine the amount of delivered dose as the difference between those positions.

Figure 26:
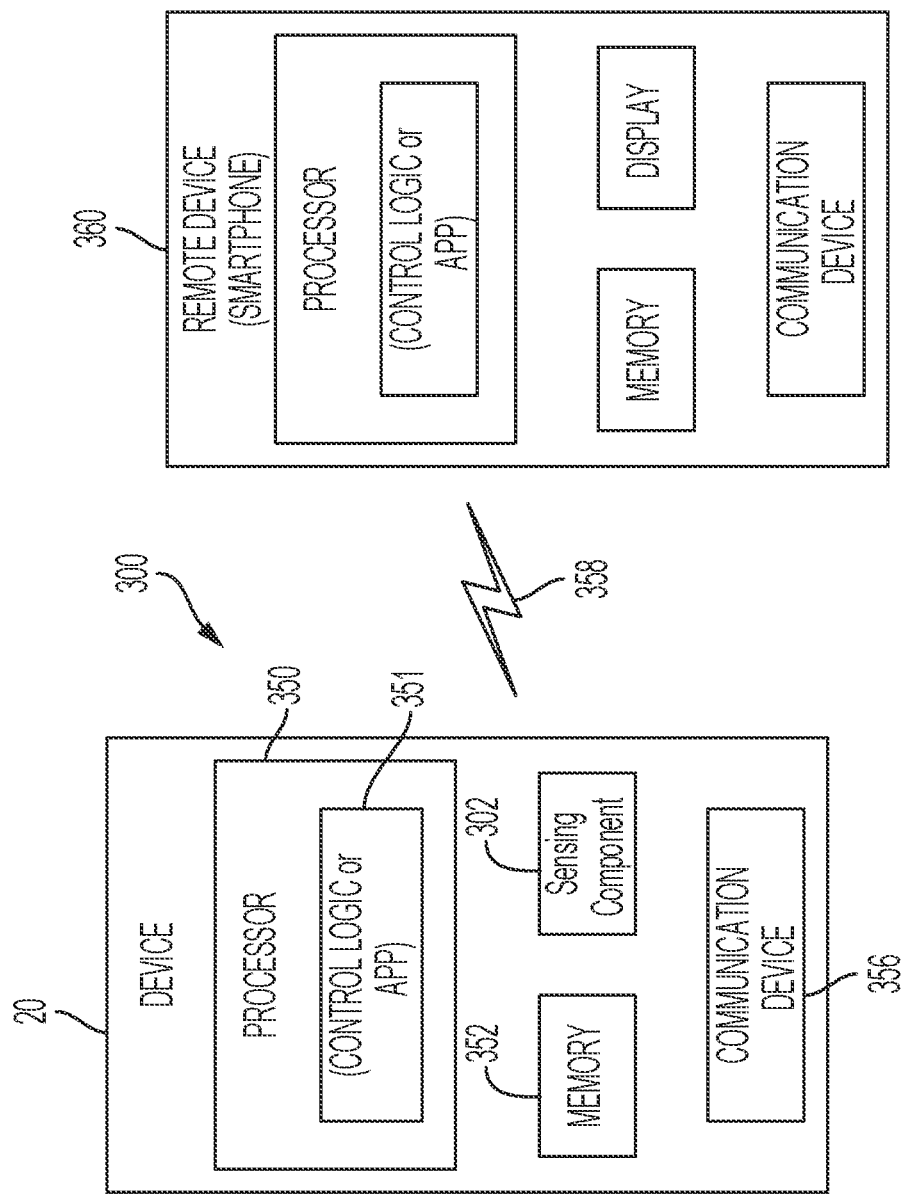
FIG. 26 is a block-diagram illustration of a medication delivery device communicating data to a remote device.

FIG. 25 illustrates one example of an electronics assembly 340 of the system 300 that can be integrated within the device that is used for dose detection. The electronics assembly 340 may include a printed circuit board (PCB) 342 having a plurality of electronic components. The electronics assembly includes the sensing component, such as electromechanical switch 320, operatively communicating with a processor 350 (shown in FIG. 26) for receiving signals from the sensor representative of the sensed relative longitudinal displacement. The electronics assembly further includes the other components, such as shown in FIG. 26. The assembly includes a battery 344, illustratively a coin cell battery, for powering the components. The processor of the microcontroller includes control logic operative to perform the operations described herein, including detecting a dose delivered by medication delivery device based on a detected displacement of the dose setting member relative to the housing.

The term "logic" or "control logic" or "application" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

In FIG. 26, the system 300 includes at least one processor 350 that executes software and/or firmware stored in memory 352 of device 20. The software/firmware code contains instructions that, when executed by processor 350, causes system controller 310 to perform the functions described herein. The at least one processor 350 illustratively includes control logic/application 351 operative to implement the operations described herein, including detecting a dose delivered by medication delivery device based on a detected displacement of the sensed element relative to the housing/sensing element. Processor 350 may be operative to store data indicative of the detected dose amount, time, and other data, into memory 352. Memory 352 is any suitable computer readable medium that is accessible by processor 350. Memory 352 may be a single storage device or multiple storage devices, may be located internally or externally to processor 350, and may include both volatile and non-volatile media. Exemplary memory 352 includes random-access memory (RAM), read-only memory (ROM), electrically erasable programmable ROM (EEPROM), flash memory, a magnetic storage device, optical disk storage, or any other suitable medium which is configured to store data and which is accessible by processor 350. The system 300 may include a communication device 356 that is further operative to wirelessly transmit and/or receive a signal 358 representative of the detected dose to a paired remote electronic device 360, such as a user's smartphone, over a Bluetooth low energy (BLE) or other suitable short or long range wireless communication protocol, such as, for example, near-field communication (NFC), WIFI, or cellular network. Similar to the device 20, remote device 360 includes a processor, memory, communication device, and also may include a display for user interface. Remote device 360 illustratively includes a mobile device, such as a smartphone. Alternatively, any suitable computing device may be used, including but not limited to a laptop, desktop, tablet, or server computer, for example.

As described briefly above, dose detection or sensing systems can be adapted for use in variously configured medication delivery devices. For example, dose detection systems may be adapted for use with medication delivery devices that include other types of mechanical advantage structures. More specifically, dose detection systems may be adapted for use with medication delivery devices that provide a mechanical advantage via converging ramps, such as any of the devices disclosed in U.S. Patent Application Publication No. 2018/0064882, the disclosure of which is hereby incorporated by reference in its entirety for all purposes. As a more specific example and referring to FIG. 27, a medication delivery device 400 that includes a dose detection system 402 and provides a mechanical advantage via converging ramps is illustrated. Generally, the medication delivery device 400 includes a housing 404 that carries a medication cartridge 406 (which may be, for example, any of the medication cartridges described herein, including the cartridge 48), a mechanical advantage-facilitating drive mechanism 408 for delivering one or more doses of medication from the medication cartridge 406, and the dose detection system 402. The housing 404 includes, for example and as illustrated, a housing front piece 410 and a housing back piece 412 that together carry the drive mechanism 408. The housing front piece 410 and the housing back piece 412 also couple to a cartridge retainer 414 that removably carries the medication cartridge 406. The cartridge retainer 414 carries a removable cap 416, which is removable by a user to facilitate delivering one or more doses of the medication from the medication cartridge 406.

Figure 27:
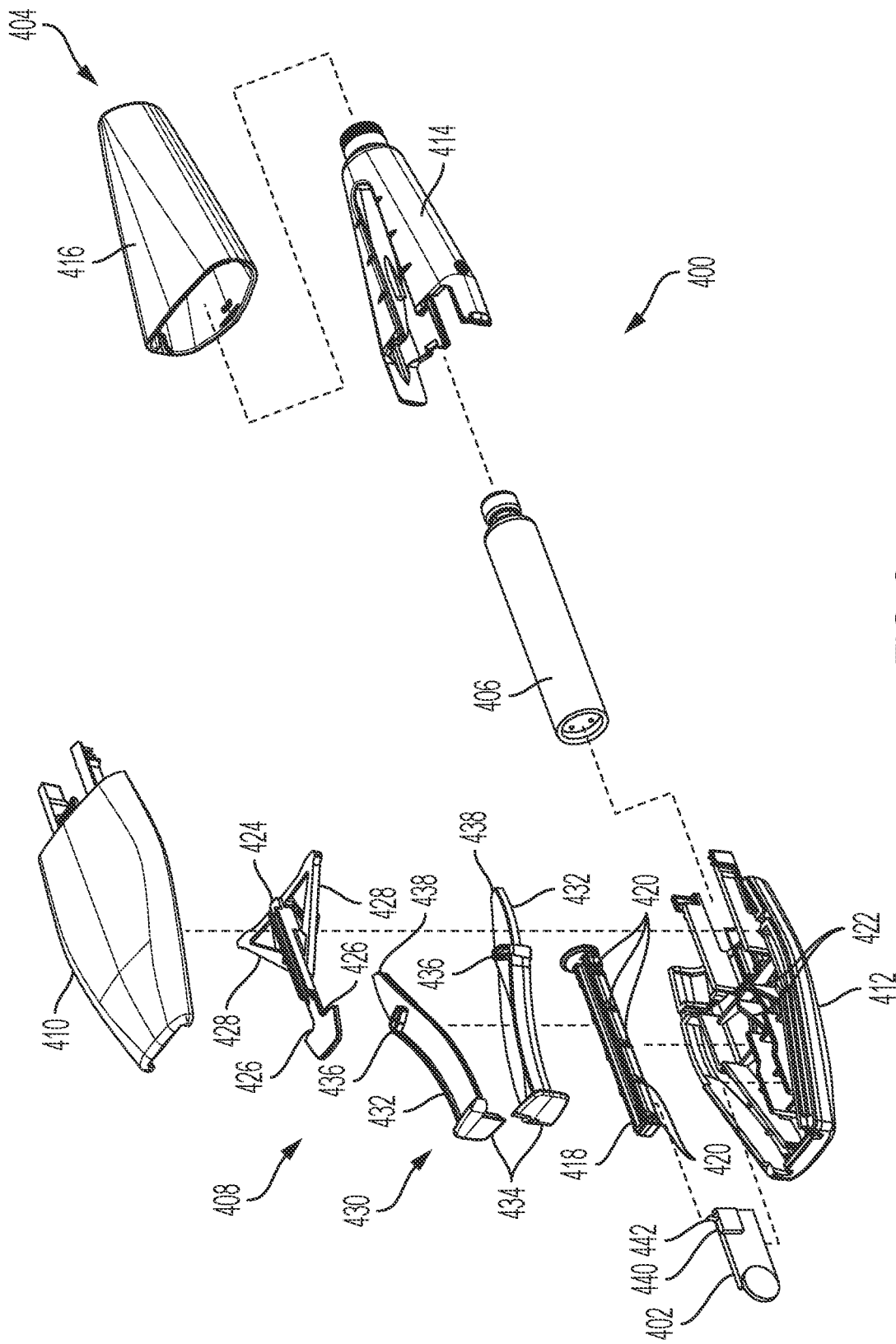
FIG. 27 is an exploded part perspective view of another example of a medication delivery device including a dose detection system.

With continued reference to FIG. 27, the drive mechanism 408 includes an elongated drive element or plunger member 418 that is translatably drivable to cause the medication cartridge 406 to deliver one or more doses of medication therefrom. As illustrated, the plunger member 418 may be unidirectionally driven relative to the housing 404. More specifically, the plunger member 418 may be drivable in a direction toward the medication cartridge 406 (that is, in a distal direction) but inhibited from moving in an opposite direction (that is, in a proximal direction). To facilitate this motion, the plunger member 418 may include a plurality of ratchet teeth 420 that engage pawls 422 of the housing 404. In addition and as described in further detail below, the plunger member 418 also operatively couples to the dose detection system 402.

With further reference to FIG. 27, the drive mechanism 408 also includes a driver or drive element 424 that is translatably carried in the housing 404. The drive element 424 is configured to unidirectionally drive the plunger member 418 relative to the housing 404. That is, the drive element 424 (1) moves together with and drives the plunger member 418 distally toward the medication cartridge 406, and (2) translates proximally relative to the plunger member 418. To facilitate this motion, the drive element 424 includes pawls (not shown) that engage the ratchet teeth 420 of the plunger member 418. The drive element 424 also includes pull surfaces 426, which, as described in further detail below, facilitate driving the drive element 424. The drive element 424 further includes ramp surfaces 428, which, as described in further detail below, facilitate providing a mechanical advantage for delivering one or more doses of the medication from the medication cartridge 406.

With continued reference to FIG. 27, the drive mechanism 408 further includes an actuator 430 that is movably operable by a user. The actuator 430 includes two arms 432 that are pivotably coupled at their proximal ends 434. The actuator arms 432 each include an intermediate glide 436 and a distal glide 438 that are configured to engage the drive element 424, as described in further detail below.

Figure 28:
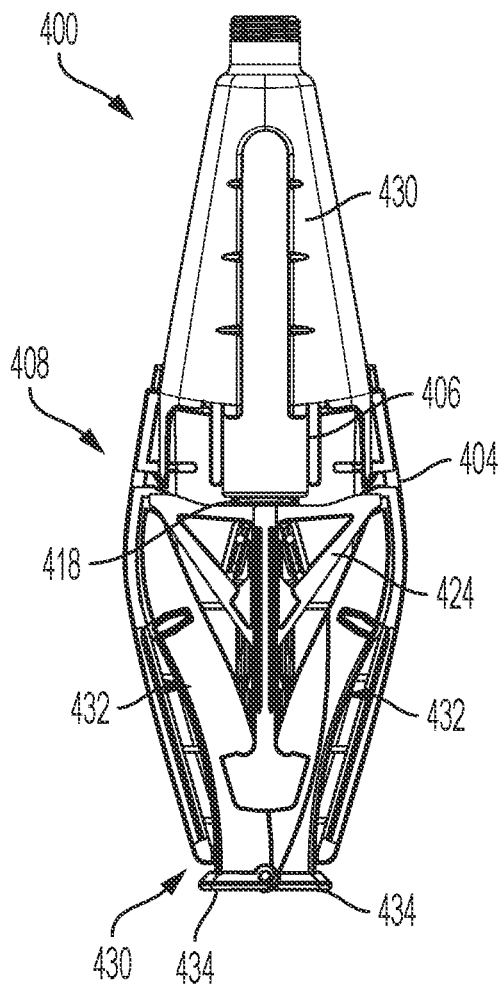
FIG. 28 is a front view of the medication delivery device of FIG. 27 prior to delivering a dose of medication and with a cap and a front distal housing piece removed.
Figure 29:
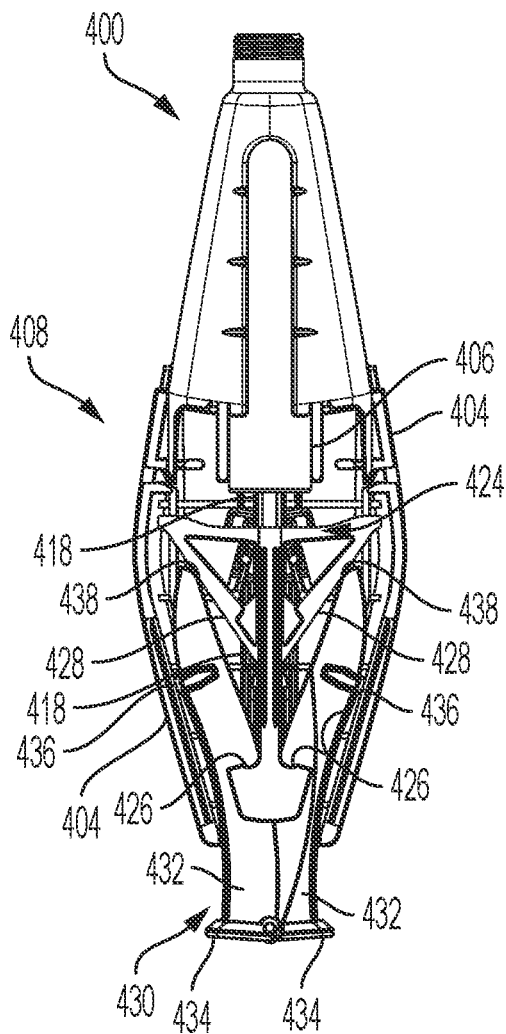
FIG. 29 is a front view of the medication delivery device of FIG. 27 during a dose delivery operation with a cap and a front distal housing piece removed.

Referring now to FIGS. 28 and 29, operation of the drive mechanism 408 of the medication delivery device 400 is generally described. FIG. 28 illustrates the drive mechanism 408 prior to delivering a dose of medication. From this position, a user proximally pulls on the proximal ends 434 of the actuator arms 432, or in a dose setting direction. As shown in FIG. 29, the housing 404 forces the actuator arms 432 to pivot toward each other. Upon continued proximal movement of the actuator 430 in the dose setting direction (movement not specifically shown), the intermediate glides 436 of the actuator arms 432 engage the pull surfaces 426 of the drive element 424. The drive element 424 then moves proximally with the actuator 430, and the plunger member 418 remains stationary relative to the housing 404 (due to the ratchet teeth 420 of the plunger member 418 and the pawls 422 of the housing 404 (both shown elsewhere)). From this position, the user then pushes the actuator 430 distally, or in a dose delivery direction. This action drives the drive element 424 distally, albeit over a smaller distance (and, consequently, at a slower rate) because the distal glides 438 of the actuator arms 432 slide over the ramp surfaces 428 of the drive element 424. This interaction between the actuator arms 432 and the drive element 424 provides a mechanical advantage—that is, the drive element 424 drives the plunger member 418 with an increased force (via the pawls of the drive element 424 (not shown) and the ratchet teeth 420 of the plunger member 418 (shown elsewhere)). Upon continued distal movement of the actuator 430 in the dose delivery direction, the plunger member 418 causes the medication cartridge 406 to deliver a dose of medication therefrom, and the medication delivery device 400 generally returns to the position shown in FIG. 28. More specifically, the actuator arms 432 and the drive element 424 return to the position shown in FIG. 28, although the plunger member 418 remains distally advanced. Operation may be repeated to deliver additional doses of medication until the medication cartridge 406 is depleted and/or the plunger member 418 reaches an end of its range of motion.

Figure 30A:
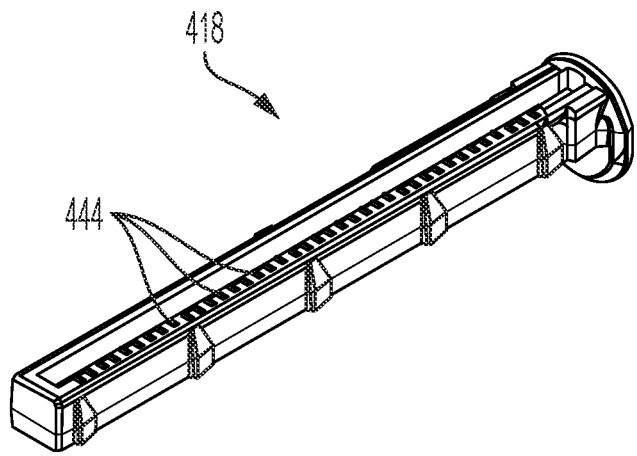
FIGS. 30a-30b are opposite end perspective views of a plunger member of the medication delivery device of FIG. 27.
Figure 30B:
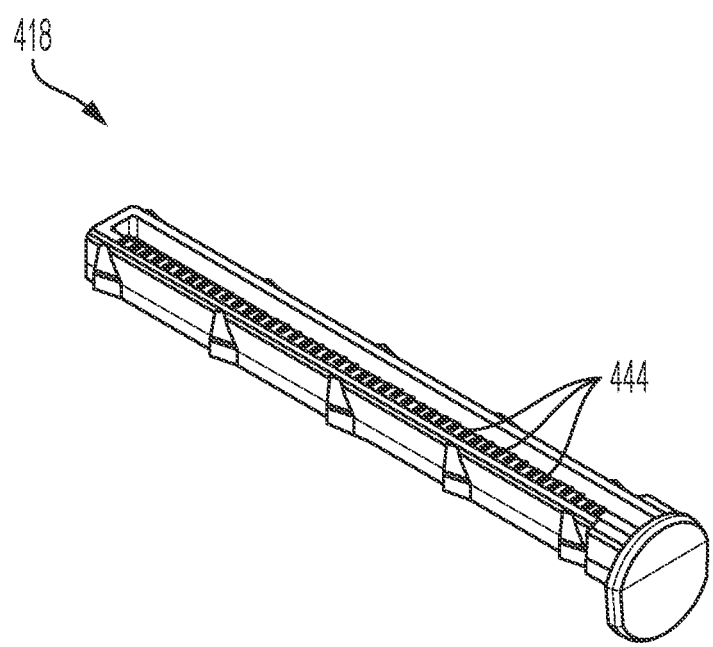

The dose sensing system 402 generally includes a sensing component and a sensed component, and the sensing component detects movement of the sensed component to determine the amount of a dose delivered by the medication delivery device 400. As shown in FIG. 27, the sensing component may include an electromechanical switch 440 having a trigger arm 442. The trigger arm 442 may be movable between two or more positions to generate an electrical actuation signal. Referring to FIGS. 30a-30b, the plunger member 418 includes a plurality of sensed teeth 444 that form the sensed component. Sensed teeth 444 may be applied along an endwall of the side wall of the plunger member, or alternatively, may be disposed along a bottom wall of the cavity defined by the endwalls, similar to how the teeth are disposed in FIGS. 6 and 6a. Generally, the electromechanical switch 440 and the sensed teeth 444, and other components of the dose detection system 402, may be similar to the components of the dose detection system shown in FIGS. 24-26. For example, the trigger arm 442 may be actuated by movement of the sensed teeth 444 against the trigger arm 442 and, after a sensed tooth 444 passes beyond the trigger arm 442, the trigger arm 442 is biased to return to its initial position. A single actuation and return of the trigger arm 442 may be recognized by the dose detection system 402 as a single count. Dose detection may be achieved by counting increments (or a total number of sensed teeth 444 triggering the switch 440) to determine a delivered dose amount. The delivered dose amount may be indicated, displayed and/or communicated via an external device (not shown), such as a smartphone or a server.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

Various aspects are described in this disclosure, which include, but are not limited to, the following aspects:

1. A medication delivery device, including: a housing defined about a longitudinal axis, the housing including one or more housing rack teeth; a plunger having an elongated body with an end to drive a piston disposed within a medication cartridge barrel, the body including a plurality of ratchet teeth disposed longitudinally spaced from one another; a plunger drive system configured to distally advance the plunger, the plunger drive system including an output drive member having one or more pawled ends movably coupled with the ratchet teeth of the plunger, the output drive member having one or more drive teeth, at least one pinion drive engaged with the drive teeth of the output drive member and the housing rack teeth of the housing, and an actuator having a coupling end coupled to the at least one pinion drive, the actuator having a unitary piece body extending between a button end and the coupling end disposed within the housing, the actuator longitudinally movable between an extended position for dose setting and a retracted position for dose delivery, wherein, in response to movement of the actuator to the extended position from the retracted position, rotation of the at least one pinion drive in a first direction along the drive teeth is configured to axially translate the output drive member relative to the plunger, with the one or more pawled ends of the output drive member sliding along the ratchet teeth of the plunger, wherein, in response to movement of the actuator to the retracted position from the extended position, rotation of the at least one pinion drive in a second direction along the drive teeth is configured to axially translate the output drive member, with the one or more pawled ends of the output drive member in engagement with the ratchet teeth of the plunger to prevent the output drive member from translating axially relative to the plunger, thereby advancing the plunger in a distal direction.

2. A medication delivery device, including: a housing defined about a longitudinal axis; a plunger having an elongated body with an end to drive a piston disposed within a medication cartridge barrel; a plunger drive system configured to distally advance the plunger, the plunger drive system including an actuator longitudinally movable between a fully extended position for dose setting and a retracted position for dose delivery; and a rotary dose selector rotatable to a first position to allow the actuator to move to the fully extended position for a full dose delivery, and rotatable to another position to place a tang in a position for engagement with the actuator to inhibit the actuator from moving to the fully extended position for a partially full dose delivery.

3. A medication delivery device, including: a housing defined about a longitudinal axis; a plunger having an elongated body with an end to drive a piston disposed within a medication cartridge barrel, the body including a plurality of ratchet teeth disposed longitudinally spaced from one another; a plunger drive system configured to distally advance the plunger, the plunger drive system including an output drive member having one or more pawled ends movably coupled with the ratchet teeth of the plunger, and an actuator longitudinally movable between an extended position for dose setting and a retracted position for dose delivery, wherein the output drive member includes a tab, and the plunger defines a longitudinal slot configured to receive the tab, the longitudinal slot defined at least in part by a proximal lip, wherein, in response to movement of the actuator to the extended position from the retracted position during dose setting, the plunger is configured to remain stationary, wherein, in response to movement of the actuator to the retracted position from the extended position during dose delivery, the plunger is configured to distally advance in a distal direction, wherein the tab is configured to contact the proximal lip of the longitudinal slot during dose setting to prevent relative movement between the output drive member and the plunger to indicate the medication delivery device is empty of medication.

4. A medication delivery device, including: a housing defined about a longitudinal axis, the housing including one or more housing rack teeth; a linearly displaceable plunger having an elongated body with an end to drive a piston disposed within a medication cartridge barrel, the body including a plurality of sensed teeth disposed longitudinally spaced from one another; a plunger drive system configured to distally advance the plunger, the plunger drive system including an output member movably coupled with the plunger, and an actuator having a coupling end coupled to the output drive member, the actuator longitudinally movable between an extended position for dose setting and a retracted position for dose delivery; a dose detection system including an electronics assembly including a switch disposed within the housing to detect the sensed teeth during movement of the plunger, a processor in communication with the switch and configured to receive a position signal based on a number of times one of the plurality of sensed teeth contacts the switch, wherein, in response to movement of the actuator to the extended position from the retracted position, the output drive member is configured to move relative to the plunger to a set position along the plunger, and wherein, in response to movement of the actuator to the retracted position from the extended position, the output drive member is configured to distally advance the plunger relative to the housing in a distal direction.

5. The device of any one of the preceding aspects, where the device includes a medication.

6. The device of any one of the preceding aspects, wherein a surface of the actuator is slidably engaged along a surface of the output drive member.

7. The device of any one of the preceding aspects, wherein one of the actuator or the output drive member includes a guide element, and the other of the actuator or the output drive member includes a rail element in slidable contact with the guide element.

8. The device of aspect 7, wherein the actuator includes the rail element, and the output drive member includes the guide element.

9. The device of aspect 8, wherein the guide element includes a pair of axially extending parallel guide ribs extending along the output drive member, and a lower surface of actuator defines the rail element that is sized to fit within a space defined by the guide ribs.

10. The device of aspect 9, wherein the actuator includes a lateral shelf extending laterally from one or both sides of the actuator, the lateral shelf disposed in between an upper surface and a lower surface of the actuator and is in sliding contact with an upper surface of the guide ribs.

11. The device of any one of the preceding aspects, wherein the at least one pinion drive includes a first pinion drive and a second pinion drive disposed along opposite sides of the output drive member, wherein the drive teeth includes a first rack and a second rack defined by the output drive member, wherein the first pinion drive member is engaged with the first rack, and the second pinion drive member is engaged with the second rack.

12. The device of aspect 11, wherein the actuator includes a first slot receiving a pin of the first pinion drive member, and a second slot receiving a pin of the second pinion drive member.

13. The device of any one of the preceding aspects, wherein the output drive member is defined by a U-shaped body to define a plunger member receiving passage receiving the plunger, wherein the U-shaped body includes a pair of parallel sides interconnected by a third side, wherein each of the parallel sides include one of the pawled end.

14. The device of aspect 13, wherein the third side of the U-shaped body includes a tab, wherein the plunger defines a longitudinal slot configured to receive the tab, the longitudinal slot defined by a proximal lip configured to contact the tab to prevent further relative movement between the output drive member and the plunger when the delivery device is empty of medication.

15. The device of any one of the preceding aspects further including a load brake pawl and teeth mechanism configured to inhibit movement of the actuator when an input force to the actuator is greater than a predetermined force.

16. The device of aspect 15, wherein the load brake pawl and teeth mechanism includes a flexible brake element located between the button end and coupling end, that is radially movable to engage a brake element defined by the housing when the input force is greater than the predetermined force.

17. The device of aspect 16, wherein the actuator includes the flexible brake element having a brake pawl configured to engage a brake tooth of the brake element.

18. The device of aspect 16, wherein the actuator includes a first flexible brake element and a second flexible brake element coupled to and disposed along opposite sides of a rigid body element of the actuator between the button end and the coupling end, the housing includes a first brake element and a second brake element, each of the first and second brake elements including a plurality of ratchet brake teeth, wherein, in response to the input force to the actuator being greater than the predetermined force, the first and second flexible brake elements radially flex inwardly to engage the ratchet brake teeth of the corresponding first and second brake elements to inhibit further distal movement of the actuator, wherein, in response to the input force to the actuator being less than the predetermined force, the first and second flexible brake elements have a natural configuration to clear the ratchet brake teeth of the corresponding first and second brake elements to allow for further distal movement of the actuator.

19. The device of any one of the preceding aspects, wherein the extended position of the actuator includes a fully extended position for a full dose setting, and the device further including a dose selector to allow the actuator to move to a dose set position that is less than the fully extended position.

20. The device of aspect 19, wherein the dose selector includes at least one axially extending tang that is selectively movable to engage a bump protrusion disposed along the actuator.

21. The device of aspect 20, wherein the dose selector includes a dose knob having an interior surface that includes the at least one axially extending tang, the dose knob being rotatable to selectively engage the bump protrusion with the at least one axially extending tang, the bump protrusion disposed along an upper surface of the actuator.

22. The device of any one of the preceding aspects further including a dose detection sensor system configured to detect a dose delivery.

23. The device of aspect 22, wherein the dose detection sensor system includes a plurality of sensed teeth defined by the plunger, and a measurement sensor coupled to the housing and configured to detect in increments the sensed teeth during movement of the plunger.

24. The device of aspect 23, wherein the dose detection sensor system includes a processor in communication with the measurement sensor including an electromechanical switch, and configured to receive a position signal indicative of each time one of the plurality of sensed teeth contacts the electromechanical switch.

25. The device of any one of the preceding aspects, wherein the plunger drive system includes a pinion drive element configured to be driven by the actuator, the pinion drive element coupled to the output drive member via a coupling means to allow transfer of force from the actuator to the output drive member.

26. A medication delivery device configured to carry a medication cartridge, the medication cartridge carrying a medication, the medication delivery device including: a housing configured to carry the medication cartridge; an actuator carried by the housing, the actuator being movable relative to the housing in a dose setting direction and an opposite dose delivery direction; a drive element carried by the housing, the drive element being movable relative to the housing in a first direction and a second direction, the second direction being opposite the first direction; a mechanical advantage structure coupling the actuator to the drive element, the mechanical advantage structure being configured such that (1) upon application of a first force to the actuator to move the actuator in the dose delivery direction, the drive element moves in the first direction with a second force, the second force being greater than the first force, and (2) upon movement of the actuator in the dose setting direction, the drive element moves in the second direction; a plunger member carried by the housing, the plunger member being movable relative to the housing in the first direction, and the plunger member being driven in the first direction upon movement of the drive element in the first direction to cause the medication cartridge to deliver a dose of the medication therefrom; and a dose detection system configured to detect delivery of the dose of the medication from the medication cartridge.

27. The device of aspect 26, wherein the dose detection system detects at least one of a position and movement of the plunger member to thereby detect delivery of the dose of the medication from the medication cartridge.

28. The device of aspect 27, wherein the dose detection system includes a plurality of teeth carried by the plunger member and a sensor carried by the housing, the sensor configured to detect the plurality of teeth.

29. The device of aspect 28, wherein the sensor includes a switch configured to engage and be actuated by the plurality of teeth, and the switch configured to send a signal when one of the plurality of teeth actuates the switch.

30. The device of aspect 29, wherein the plunger member is elongated in a longitudinal direction substantially parallel to the first direction and the second direction, and the plurality of teeth are spaced apart in the longitudinal direction.

I claim:

1. A medication delivery device, comprising:
   a housing defined about a longitudinal axis;
   a medication cartridge comprising a piston disposed therein;
   a plunger having an elongated body with an end to drive the piston within the medication cartridge, the elongated body including a plurality of ratchet teeth disposed longitudinally spaced from one another;
   a plunger drive system configured to distally advance the plunger, the plunger drive system including an output drive member having one or more pawled ends movably coupled with the ratchet teeth of the plunger, at least one pinion drive operably engaged between the output drive member and the housing, and an actuator having a coupling end coupled to the at least one pinion drive and a button end, the actuator longitudinally movable between an extended position and a retracted position, the actuator comprising a bump protrusion; and
   a dose selector configured to allow the actuator to move to a lesser dose set position that is less than the extended position that defines a full dose setting, wherein the dose selector comprises at least one axial tang, wherein the dose selector is rotatable to a first position to allow the actuator to move to the extended position that defines the full dose setting and a second position to allow the actuator to move to the lesser dose set position in response to engagement between the at least one axial tang and the bump protrusion of the actuator,
   wherein, in response to movement of the actuator to the extended position or the lesser dose set position from the retracted position, rotation of the at least one pinion drive is in a first direction to axially translate the output drive member relative to the plunger, with the one or more pawled ends of the output drive member sliding along the ratchet teeth of the plunger,
   wherein, in response to movement of the actuator to the retracted position from the extended position, rotation of the at least one pinion drive is in a second direction to axially translate the output drive member, with the one or more pawled ends of the output drive member in engagement with the ratchet teeth of said plunger, thereby advancing the plunger in a distal direction.

2. The device of claim 1, wherein a surface of the actuator is slidably engaged along a surface of the output drive member.

3. The device of claim 1, wherein one of the actuator or the output drive member includes a guide element, and the other of the actuator or the output drive member includes a rail element in slidable contact with the guide element.

4. The device of claim 3, wherein the actuator includes said rail element, and the output drive member includes said guide element.

5. The device of claim 1, wherein the at least one pinion drive includes a first pinion drive and a second pinion drive disposed along opposite sides of the output drive member, wherein the output drive member includes a first rack and a second rack, wherein the first pinion drive is engaged with the first rack, and the second pinion drive is engaged with the second rack.

6. The device of claim 5, wherein the actuator includes a first slot receiving a pin of the first pinion drive, and a second slot receiving a pin of the second pinion drive.

7. The device of claim 1, wherein the output drive member is defined by a U-shaped body to define a plunger member receiving passage receiving the plunger, wherein the U-shaped body includes a pair of parallel sides interconnected by a third side.

8. The device of claim 7, wherein said third side of said U-shaped body includes a tab, wherein the plunger defines a longitudinal slot configured to receive said tab, the longitudinal slot defined by a proximal lip configured to contact the tab to prevent further relative movement between the output drive member and the plunger when the delivery device is empty of medication.

9. The device of claim 1, wherein the dose selector comprises a dose knob having an interior surface that includes said at least one axially extending tang and a tangless region.

10. The device of claim 9, wherein said at least one axially extending tang comprises a first tang having a length sized to correspond to a travel distance of one ratchet teeth less than a number of ratchet teeth for the full dose setting.

11. The device of claim 10, wherein said at least one axially extending tang comprises a second tang having a length sized to correspond to a travel distance of two ratchet teeth less than the number of ratchet teeth for the full dose setting.

12. The device of claim 9 wherein the dose knob includes an internal lip having a locking region, wherein when the dose knob is at a locked position, the locking region of the internal lip is configured to physically block the actuator from moving to the extended position.

13. The device of claim 1 further comprising a load brake pawl and teeth mechanism configured to inhibit movement of the actuator when an input force to the actuator is greater than a predetermined force.

14. The device of claim 13, wherein the load brake pawl and teeth mechanism includes a flexible brake element located between the button end and the coupling end, that is radially movable to engage a brake element defined by the housing when the input force is greater than the predetermined force.

15. The device of claim 1, further comprising a dose detection sensor system that includes a plurality of sensed teeth defined by the plunger, and a measurement sensor coupled to the housing and configured to detect in increments the sensed teeth during movement of the plunger during dose delivery.

16. The device of claim 15, wherein the dose detection sensor system includes a processor in communication with the measurement sensor comprising an electromechanical switch, and configured to receive a position signal indicative of each time one of the plurality of sensed teeth contacts the electromechanical switch.

17. The device of claim 1, wherein the medication cartridge contains a medication.

18. A method of delivering a medication, comprising:
moving an actuator of a medication delivery device longitudinally to an extended position from a retracted position, thereby causing rotation of at least one pinion drive in a first direction which axially translates an output drive member relative to a plunger, with one or more pawled ends of the output drive member sliding along a plurality of ratchet teeth of the plunger, the medication delivery device comprising a housing defined about a longitudinal axis, a medication cartridge holding the medication and comprising a piston disposed therein and an outlet, the plunger having an elongated body with an end to drive the piston within the medication cartridge, the elongated body including the plurality of ratchet teeth disposed longitudinally spaced from one another, the at least one pinion drive operably engaged between the output drive member and the housing, the actuator having a coupling end coupled to the at least one pinion drive and a button end,
moving the actuator longitudinally to the retracted position from the extended position, thereby causing rotation of the at least one pinion drive in a second direction which axially translates the output drive member, with the one or more pawled ends of the output drive member in engagement with the ratchet teeth of said plunger for advancing the plunger and thus the piston in a distal direction to expel the medication from the outlet.

19. The method of claim 18, wherein the actuator includes a bump protrusion, and the device includes a dose selector configured to allow the actuator to move to a lesser dose set position that is less than the extended position that defines a full dose setting, wherein the dose selector comprises at least one axial tang, the method further comprising:
prior to the moving the actuator to the extended position step, rotating the dose selector to a first position to allow the actuator to move to the extended position that defines the full dose setting or to a second position to allow the actuator to move to the lesser dose set position in response to engagement between the at least one axial tang and the bump protrusion of the actuator.

20. The method of claim 18, further comprising:
braking the movement of the actuator to the retracted position when the input force to the actuator is greater than the predetermined force.

* * * * *

UNITED STATES PATENT AND TRADEMARK OFFICE
CERTIFICATE OF CORRECTION

PATENT NO. : 12,011,574 B2
APPLICATION NO. : 17/508494
DATED : June 18, 2024
INVENTOR(S) : Jared A. Judson Page 1 of 1

It is certified that error appears in the above-identified patent and that said Letters Patent is hereby corrected as shown below:

In the Specification

In Column 1, Line 8, delete "11,179,522" and insert -- 11,179,522, --, therefor.

In Column 1, Line 9, delete "s. 371" and insert -- §371 --, therefor.

Signed and Sealed this
Fifth Day of November, 2024

Katherine Kelly Vidal
*Director of the United States Patent and Trademark Office*